(12) United States Patent
Boger

(10) Patent No.: US 6,891,043 B2
(45) Date of Patent: May 10, 2005

(54) INHIBITORS OF FATTY ACID AMIDE HYDROLASE

(75) Inventor: Dale L. Boger, La Jolla, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 10/267,530

(22) Filed: Oct. 8, 2002

(65) Prior Publication Data

US 2003/0092734 A1 May 15, 2003

Related U.S. Application Data

(62) Division of application No. 09/536,842, filed on Mar. 27, 2000, now Pat. No. 6,462,054.

(51) Int. Cl.[7] ............... C07D 498/04; C07D 263/57
(52) U.S. Cl. ............... 546/115; 544/184; 544/236; 544/255; 544/350; 548/180; 548/217; 548/218; 548/309.4
(58) Field of Search ............... 548/180, 217, 548/218, 309.4; 546/115; 544/184, 236, 255, 350

(56) References Cited

PUBLICATIONS

Chemical Abstracts Online, Registry No. 76115–66–7.*
Chemical Abstracts Online, Registry No. 225108–75–5.*
Chemical Abstracts Online, Registry No. 115951–83–2.*
Chemical Abstracts Online,Registry No. 38866–32–9.*
Chem. Abstracts Online, Registry No. 37547–85–6.*
Chem. Absracts Onlinem Registry No. 27411–62–7.*
Chemical Abstracts Online, Registry No. 76115–66–7.
Chemical Abstracts Online, Registry No. 225108–72–5.
Chemical Abstracts Online, Registry No. 115951–83–2.
Chemical Abstracts Online, Registry No. 38866–32–9.
Chemical Abstracts Online, Registry No. 37547–85–6.
Chemical Abstracts Online, Registry No. 27411–62–7.

* cited by examiner

*Primary Examiner*—Bernard Dentz
(74) *Attorney, Agent, or Firm*—Donald G. Lewis

(57) ABSTRACT

Potent inhibitors of fatty acid amide hydrolase (FAAH) are constructed having $K_1$'s below 200 pM and activities $10^2$–$10^3$ times more potent than the corresponding trifluoromethyl ketones. The potent inhibitors combine several features, viz.: 1.) an α-keto heterocylic head group; 2.) a hydrocarbon linkage unit employing an optimal C12–C8 chain length; and 3.) a phenyl or other π-unsaturation corresponding to the arachidonyl $\Delta^{8,9}/\Delta^{11,12}$ and/or oleyl $\Delta^{9,10}$ positions. A preferred α-keto heterocylic head group is α-keto N4 oxazolopyridine, with incorporation of a second weakly basic nitrogen. Fatty acid amide hydrolase is an enzyme responsible for the degradation of oleamide (an endogenous sleep-inducing lipid) and anandamide (an endogenous ligand for cannabinoid receptors).

3 Claims, 19 Drawing Sheets

α-Keto Heterocycle Inhibitors of Fatty Acid Amide Hydrolase (FAAH)

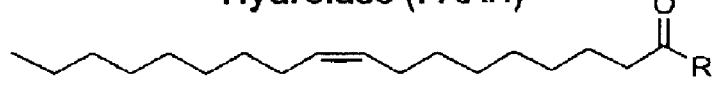

| compd | R | $K_i$, μM | compd | R | $K_i$, μM |
|---|---|---|---|---|---|
| 3 | $CF_3$ | 0.082 ±0.012 | | $CH_3$ | > 100 |
| 4 | H | 8.5 ±2.5 | 5 | $CH_2Br$ | 1.0 ±0.2 |
| 6 | $CO_2Et$ | 0.50 ±0.02 | 7 | $CONH_2$ | 0.90 ±0.1 |
| 8 | thiazole | > 100 | 15 | phenyl | > 100 |
| 9 | N-Me imidazole | > 100 | 16 | pyridine | > 100 |
| 10 | oxazole | 0.017 ±0.002 | 17 | pyridazine | 0.13 ±0.02 |
| 11 | | 4.5 ±1.5 | | | |
| 12 | tetrazole NH | 9.8 ±2.8 | 18 | pyrimidine | 0.11 ±0.02 |
| 13 | tetrazole N-Me | 3.7 ±0.9 | 19 | pyrazine | 0.54 ±0.14 |
| 14 | triazole N-NMe | 0.065 ±0.02 | 20 | pyrimidine | 2.5 ±0.2 |
| 21 | benzimidazole NH | > 100 | 22 | benzimidazole N-Me | > 100 |
| 23 | benzoxazole | 0.37 ±0.13 | 24 | benzothiazole | > 100 |

- Potency approaches that of trifluoromethyl ketone
- Potency increases with additional basic nitrogen

Figure 3

Substituted α-Keto Benzoxazole Inhibitors of Fatty Acid Amide Hydrolase (FAAH)

| compd | R | $K_i$, μM | compd | R | $K_i$, μM |
|---|---|---|---|---|---|
| 25 | 4-Me-benzoxazole | > 100 | 26 | 5-Me-benzoxazole | > 100 |
| 27 | 6-Me-benzoxazole | > 100 | 28 | 7-Me-benzoxazole | 13 ±3 |

- Sensitive to steric interactions surrounding active site
- Defines limits to depth and width of FAAH active site

Figure 4

α-Keto Oxazolopyridine Inhibitors of Fatty Acid Amide Hydrolase (FAAH)

| compd | R | $K_i$, μM | compd | R | $K_i$, μM |
|---|---|---|---|---|---|
| 29 | oxazolo[4,5-b]pyridine | 0.0023 ±0.0001 | 30 | oxazolo[4,5-c]pyridine | 0.0072 ±0.0016 |
| 31 | oxazolo[5,4-c]pyridine | 0.0037 ±0.0010 | 32 | oxazolo[5,4-b]pyridine | 0.011 ±0.004 |

- Potency increases with introduction of basic nitrogen
- Potency increases ca. 200x and N4 > N6 > N5 > N7
- Relatively insensitive to location of additional nitrogen

Figure 5

Impact of Double Bond in the C18 α-Keto Heterocycle Inhibitors of FAAH

| compd | R | $K_i$, μM |
|---|---|---|
| 29 | | 0.0023 ±0.0001 |
| 33 | | 0.0032 ±0.0006 |
| 34 | | 0.011 ±0.006 |

| compd | R | $K_i$, μM |
|---|---|---|
| 17 | | 0.13 ±0.02 |
| 35 | | 0.15 ±0.02 |
| 36 | | 0.70 ±0.03 |

| compd | R | $K_i$, μM |
|---|---|---|
| 23 | | 0.37 ±0.13 |
| 37 | | 2.4 ±0.5 |

- C18 $\Delta^{9,10}$: Z (cis) > E (trans) > saturated

Figure 6

Arachidonyl-based α-Keto Heterocycle Inhibitors of
Fatty Acid Amide Hydrolase (FAAH)

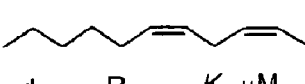

| compd | R | $K_i$, μM | compd | R | $K_i$, μM |
|---|---|---|---|---|---|
| 38 | (oxazolopyridine) | 0.001 ±0.0002 | 39 | (oxazolopyridine) | 0.002 ±0.001 |
| 40 | (oxazolopyridine) | ca. 0.018 unstable | - | (oxazolopyridine) | unstable |
| 41 | (pyridazine N-N) | 0.047 ±0.017 | | | |

- Potency: arachidonyl > oleyl inhibitors (2–5x)
- Stability: oleyl >> arachidonyl inhibitors

Figure 7

Modifications in the Fatty Acid Side Chain of α-Keto
Heterocycle Inhibitors of FAAH

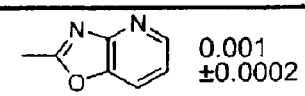

| compd | R | $K_i$, μM | compd | R | $K_i$, μM |
|---|---|---|---|---|---|
| 34 | $CH_3(CH_2)_{16}$ | 0.011 ±0.006 | 51 | $Ph(CH_2)_3$ | 0.0069 ±0.0010 |
| 42 | $CH_3(CH_2)_{14}$ | 0.0019 ±0.0002 | 52 | $Ph(CH_2)_4$ | 0.00030 ±0.00009 |
| 43 | $CH_3(CH_2)_{12}$ | 0.0017 ±0.0009 | 53 | $Ph(CH_2)_5$ | 0.00020 ±0.00005 |
| 44 | $CH_3(CH_2)_{10}$ | 0.00057 ±0.00024 | 54 | $Ph(CH_2)_6$ | 0.00028 ±0.00020 |
| 45 | $CH_3(CH_2)_8$ | 0.00075 ±0.00017 | 55 | $Ph(CH_2)_7$ | 0.00039 ±0.00006 |
| 46 | $CH_3(CH_2)_6$ | 0.00069 ±0.00015 | 56 | $Ph(CH_2)_8$ | 0.00052 ±0.00018 |
| 47 | $CH_3(CH_2)_5$ | 0.0021 ±0.0003 | | | |
| 48 | $CH_3(CH_2)_4$ | 0.015 ±0.002 | | | |
| 49 | $CH_3(CH_2)_3$ | 0.050 ±0.009 | | | |
| 50 | $CH_3$ | > 100 | | | |

Comparisons with the α-Hydroxy Heterocycle Inhibitors of Fatty Acid Amide Hydrolase (FAAH)

| compd | R | $K_i$, μM | compd | R | $K_i$, μM |
|---|---|---|---|---|---|
| 57 | benzoxazole | > 100 | 58 | benzimidazole (NH) | > 100 |
| 59 | oxazolopyridine | 1.8 ±0.4 | | | |
| 60 | CH₃(CH₂)₁₀—CH(OH)—oxazolopyridine | 1.2 ±0.2 | 61 | CH₃(CH₂)₁₆—CH₂—oxazolopyridine | > 100 |
| 62 | long alkenyl chain—CH₂—oxazolopyridine | > 100 | | | |

- Ketone >> alcohol ($10^3$x) >> alkane ($10^5$x)

Figure 9

Inhibition of Recombinant Human Fatty Acid Amide Hydrolase (FAAH)

| compd | $K_i$, μM (human) | $K_i$, μM (rat) |
|---|---|---|
| 23 | 0.073 | 0.37 |
| 29 | 0.0013 | 0.0023 |
| 53 | 0.000094 | 0.00020 |

- Relative and absolute potencies against rat and human FAAH not distinguisable

Figure 10

Alpha-functionalization of the carbonyl-containing tail.
Fluorine
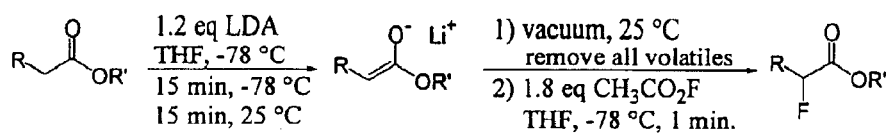
Rozen, S.; Brand, M. *Synthesis* 1985, 665-667.
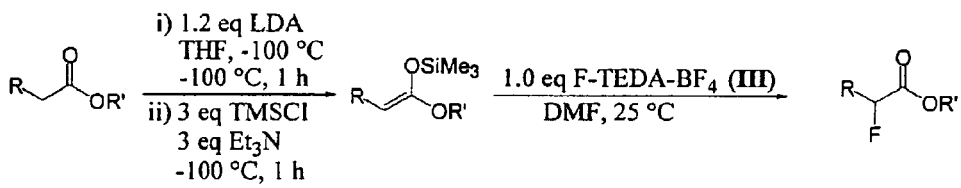
Lal, G. S. *J. Org. Chem.* 1993, *58*, 2791-2796.
α-Chiral Fluorine
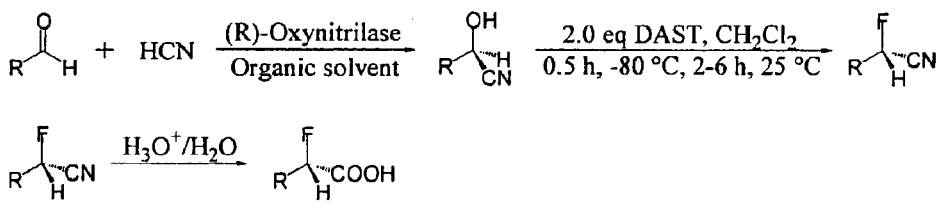
Stelzer, U.; Effenberger, F. *Tetrahedron: Asymmetry* 1993, *4*, 161-164.
Hydroxyl
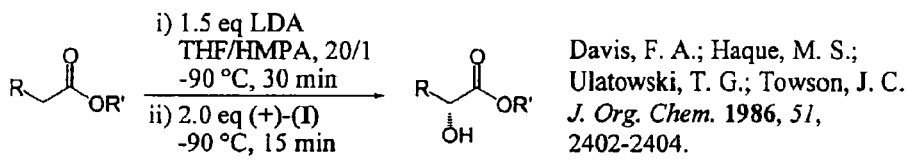
Davis, F. A.; Haque, M. S.; Ulatowski, T. G.; Towson, J. C. *J. Org. Chem.* 1986, *51*, 2402-2404.
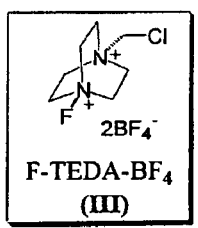
F-TEDA-BF$_4$ (III)
Trifluoromethyl
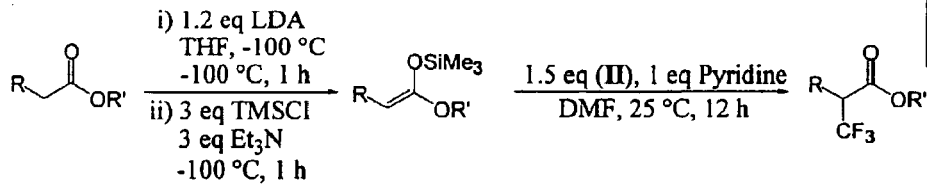
Umemoto, T.; Ishihara, S. *J. Am. Chem. Soc.* 1993, *115*, 2156-2164.
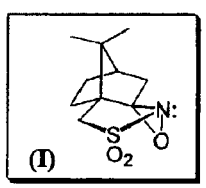
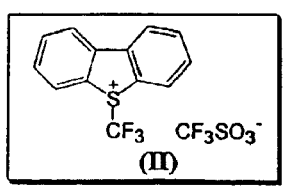
Figure 11

Alpha-functionalization of the carbonyl-containing tail.
Chlorine
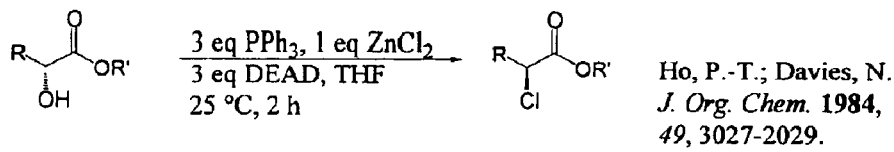
Ho, P.-T.; Davies, N. *J. Org. Chem.* 1984, *49*, 3027-2029.
α-Alkyl-α-hydroxy
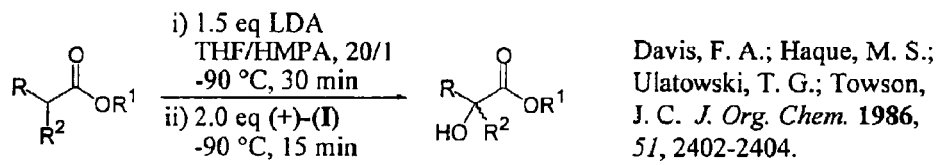
Davis, F. A.; Haque, M. S.; Ulatowski, T. G.; Towson, J. C. *J. Org. Chem.* 1986, *51*, 2402-2404.
α-Hydroxy-α-trifluoromethyl-
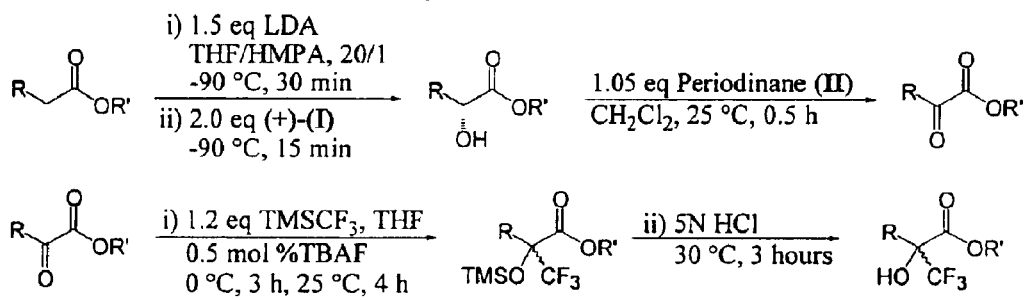
Davis, F. A.; Haque, M. S.; Ulatowski, T. G.; Towson, J. C. *J. Org. Chem.* 1986, *51*, 2402-2404.
Dess, D. B.; Martin, J. C. *J. Org. Chem.* 1983, *83*, 4155-4156.
Ramaiah, P.; Prakash, G. K. S. *Synlett* 1991, 643-644.
α-Alkyl-α-fluoro
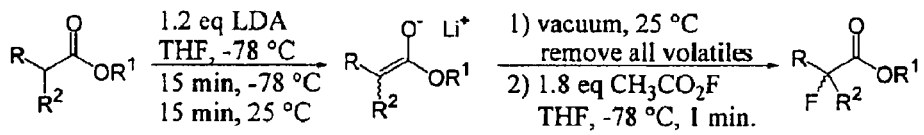
Rozen, S.; Brand, M. *Synthesis* 1985, 665-667.
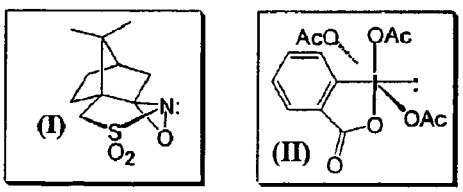
Figure 12

| Method of Acylation | Starting materials required and the source(s) for them | References for synthesizing the starting materials, or particular acylations or heterocycle formation |
|---|---|---|
| Method C from the specification | 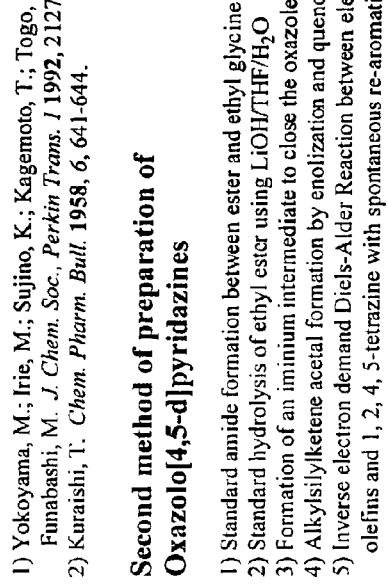 | Synthesis of Oxazolo[3, 4-d]pyridazine<br>1) Takimoto, H. H.; Denault, G. C.; Hotta, S. *J. Org. Chem.* 1965, *30*, 711-713. (Synthesis of triaminoguanidine hydrochloride)<br>2) Kröger, C. F.; Etzold, G.; Beyer, H. *Ann.* 1963, *664*, 146. (Synthesis of 4-amino-3-hydrazino-1, 2, 4-triazole)<br>3) Takimoto, H. H.; Denault, G. C. *Tetrahedron Lett.* 1966, 5369-5373. (Synthesis of 3-amino-1, 2, 4, 5-tetrazine)<br>4) Kuo, Y.-N., Chen, F.; Ainsworth, C. *J. Chem. Soc., Chem. Commun.* 1971, 136-137. (Synthesis of bis-O-trimethylsilyl-ketene acetal)<br>5) Sauer, J.; Heldmann, D. K.; Hetzenegger, J.; Krauthan, J.; Sichert, H.; Schuster, J. *Eur. J. Org. Chem.* 1998, 2885-2896. (Inverse electron-demand Diels-Alder reaction with silylenol ether)<br>6) Hierstetter, T.; Tischler, B.; Sauer, J. *Tetrahedron Lett.* 1992, *33*, 8019-8022. (Cycloaddition with bis-O-TMS ketene acetal and 3, 6-bis(carbomethoxy)-1, 2, 4, 5-tetrazine) |
| Method C from the specification | 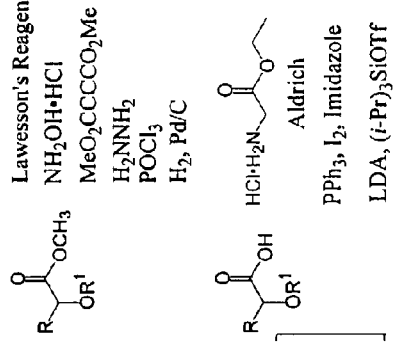 | 1) Yokoyama, M.; Irie, M.; Sujino, K.; Kagemoto, T.; Togo, H.; Funabashi, M. *J. Chem. Soc., Perkin Trans. 1* 1992, 2127-2134.<br>2) Kuraishi, T. *Chem. Pharm. Bull.* 1958, *6*, 641-644.<br><br>Second method of preparation of Oxazolo[4,5-d]pyridazines<br>1) Standard amide formation between ester and ethyl glycine<br>2) Standard hydrolysis of ethyl ester using LiOH/THF/H$_2$O<br>3) Formation of an iminium intermediate to close the oxazole ring<br>4) Alkylsilylketene acetal formation by enolization and quenching<br>5) Inverse electron demand Diels-Alder Reaction between electron-rich olefins and 1, 2, 4, 5-tetrazine with spontaneous re-aromatization after the cycloaddition.<br>Sauer, J.; Heldmann, D. K.; Hetzenegger, J.; Krauthan, J.; Sichert, H.; Schuster, J. *Eur. J. Org. Chem.* 1998, 2885-2896. |

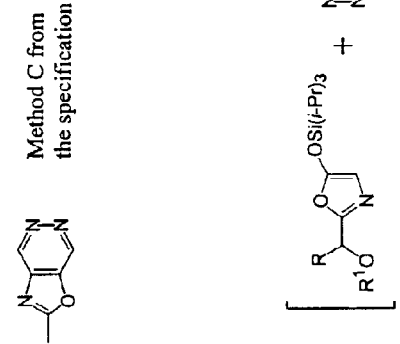

Figure 15

| Method of Acylation | Starting materials required and the source(s) for them | References for synthesizing the starting materials, or particular acylations or heterocycle formation |
|---|---|---|
| Method C | 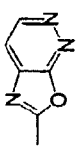 H₂N / HO | 1) Alazawe, S.; Elvidge, J. A. *J. Chem. Soc., Perkins Trans. 1* 1974, 696-698. (4-amino-6-chloropyridazin-3(2H)-one preparation)<br>2) Coates, W. J.; McKillop, A. *Heterocycles* 1993, *35*, 1313-1329. (Reduction of the chloro compound above and physical properties) |
| Method C | 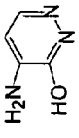 H₂N / HO | 1) Chesterfield, J. H.; McOmie, J. F. W.; Tute, M. S. *J. Chem. Soc.* 1960, 4590-4596. (Synth. of 5-BnO-4-OH-2-SH-pyrimidine, SM for below.)<br>2) McOmie, J. F. W.; Turner, A. B. *J. Chem. Soc.* 1963, 5590-5593.<br>3) Doise, M.; Dennin, F.; Blondeau, D.; Sliwa, H. *Tetrahedron Lett.* 1990, *31*, 1155-1156. (References the procedure for synth.)<br>4) Doise, M.; Blondeau, D.; Sliwa, H. *Synth. Commun.* 1992, *22*, 2891-2901. (Formation of Oxazole from 4-amino-5-hydroxypyrimidine) |
| Method C | 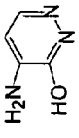 H₂N / HO | Veale, C. A.; Bernstein, P. R.; Bryant, C.; Ceccarelli, C.; Damewood, Jr., J. R.; Earley, R.; Feeney, S. W.; Gomes, B.; Kosmider, B. J.; Steelman, G. B.; Thomas, R. M.; Vacek, E. P.; Williams, J. C.; Wolanin, D. J.; Woolson, S. *J. Med. Chem.* 1995, *38*, 98-108. |
| Method C | 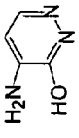 H₂N / HO | 1) Snyder, H. R.; Smith, C. W. *J. Am. Chem. Soc.* 1944, *66*, 350-351.<br>2) Schipper, E.; Day, A. R. *J. Am. Chem. Soc.* 1952, *74*, 350-353.<br>3) Muehlmann, F. L.; Day, A. R. *J. Am. Chem. Soc.* 1956, *78*, 242-244.<br>4) Lee, T.-C.; Chello, P. L.; Chou, T.-C.; Templeton, M. A.; Parham, J. C. *J. Med. Chem.* 1983, *26*, 283-286. |

Figure 16

| Method of Acylation | Starting materials required and the source(s) for them | References for synthesizing the starting materials, or particular acylations or heterocycle formation |
|---|---|---|
| 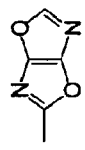 Oxazolo[5,4-d]oxazole | 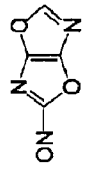 | Wardermann, W.; Von Niessen, W. *Chem. Phys.* 1992, *159*, 11-27. |
| 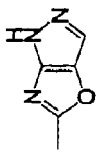 1H-Pyrazolo[4,3-d]oxazole | | Common 5,5 heteroaromatic ring system The systhesis is known in the art. |
Figure 18

Oligoethylene glycol chain analogs-Synthesis of the Oligoethylene glycol glycolic acids

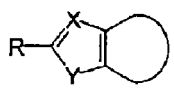

Acids that are commercially available $C_6H_8O_2$     2,4-Hexadienoic acid(sorbic acid)

$C_6H_{10}O_2$     trans-2-Hexenoic acid, trans-3-hexenoic acid, trans-2-methyl-2-pentenoic acid $C_6H_{12}O_2$     2-Ethylbutyric acid, hexanoic acid, 2-methylvaleric acid, 3-methylvaleric acid, 4-methylvaleric acid $C_7H_{10}O_2$     2,6-Heptadienoic acid, 6-heptynoic acid $C_7H_{12}O_2$     2,2-Dimethyl-4-pentenoic acid, 6-heptenoic acid $C_7H_{14}O_2$     Heptanoic acid, 2-methylhexanoic acid $C_8H_{12}O_2$     2-Octynoic acid $C_8H_{14}O_2$     3-Cyclopentylpropionic acid, 2-ethyl-2-hexenoic acid, 2-octenoic acid $C_8H_{16}O_2$     2-Ethylhexanoic acid, octanoic acid, 2-propylpentanoic acid, $C_9H_{16}O_2$     Cyclohexanepropionic acid, 4-methylcyclohexaneacetic acid $C_9H_{18}O_2$     Nonanoic acid $C_{10}H_{10}O_2$     α-Methylcinnamic acid, 2-methylcinnamic acid, 3-methylcinnamic acid, 4-methylcinnamic acid, trans-styrylacetic acid $C_{10}H_{12}O_2$     α-Methylhydrocinnamic acid, 2-methylhydrocinnamic acid, 2-phenylbutyric acid, 3-phenylbutyric acid, 4-phenylbutyric acid, 3-(p-tolyl)propionic acid $C_{10}H_{14}O_2$ $C_{10}H_{16}O_2$     Geranic acid

Figure 20

| | |
|---|---|
| $C_{10}H_{18}O_2$ | (R)- or (S)-citronellic acid, cyclohexanebutyric acid |
| $C_{10}H_{20}O_2$ | Decanoic acid |
| $C_{11}H_{10}O_2$ | 3-Methylindene-2-carboxylic acid |
| $C_{11}H_{12}O_2$ | 1, 2, 3, 4-Tetrahydro-2-naphthoic acid |
| $C_{11}H_{14}O_2$ | 5-Phenylvaleric acid |
| $C_{11}H_{16}O_2$ | |
| $C_{11}H_{18}O_2$ | 10-Undecynoic acid |
| $C_{11}H_{20}O_2$ | Cyclohexanepentanoic acid, undecylenic acid |
| $C_{11}H_{22}O_2$ | Undecanoic acid |
| $C_{12}H_{10}O_2$ | 1-Naphthylacetic acid, 2-naphthylacetic acid |
| $C_{12}H_{12}O_2$ | |
| $C_{12}H_{14}O_2$ | |
| $C_{12}H_{16}O_2$ | 3-Methyl-2-phenylvaleric acid, 6-phenylhexanoic acid |
| $C_{12}H_{18}O_2$ | 1-Adamantaneacetic acid |
| $C_{12}H_{20}O_2$ | |
| $C_{12}H_{22}O_2$ | cis-5-Decenoic acid |

Figure 21

| | |
|---|---|
| $C_{12}H_{24}O_2$ | 2-Butyloctanoic acid, lauric acid |
| $C_{13}H_{18}O_2$ | α-(tert-Butyl)hydrocinnamic acid, 4-isobutyl-α-methylphenylacetic acid |
| $C_{13}H_{26}O_2$ | Tridecanoic acid |
| $C_{14}H_{12}O_2$ | 4-Biphenylacetic acid, diphenylacetic acid |
| $C_{14}H_{24}O_2$ | Dicyclohexylacetic acid |
| $C_{14}H_{26}O_2$ | Myristoleic acid(cis-9-tetradecenoic acid) |
| $C_{14}H_{28}O_2$ | Myristic acid(tetradecanoic acid) |
| $C_{15}H_{12}O_2$ | 9-Fluoreneacetic acid, α-phenylcinnamic acid |
| $C_{15}H_{14}O_2$ | 3,3-Diphenylpropionic acid |
| $C_{15}H_{30}O_2$ | Pentadecanoic acid |
| $C_{16}H_{30}O_2$ | Palmitoleic acid(9-cis-hexadecenoic acid) |
| $C_{16}H_{32}O_2$ | 2-Hexyldecanoic acid, Palmitic acid(hexadecanoic acid) |
| $C_{17}H_{34}O_2$ | Heptadecanoic acid |

Figure 22

| | |
|---|---|
| $C_{18}H_{30}O_2$ | Linolenic acid ($CH_3(CH_2CH=CH)_3(CH_2)_7CO_2H$) |
| $C_{18}H_{32}O_2$ | Linoleic acid ($CH_3(CH_2)_3(CH_2CH=CH)_2(CH_2)_7CO_2H$) |
| $C_{18}H_{34}O_2$ | Elaidic acid ($CH_3(CH_2)_7CH=CH(CH_2)_7CO_2H$), Oleic acid(cis-9-octadecenoic acid) |
| $C_{18}H_{36}O_2$ | Stearic acid (octadecanoic acid) |
| $C_{19}H_{38}O_2$ | Nonadecanoic acid |
| $C_{20}H_{16}O_2$ | 4-(1'-Pyrene)butyric acid |
| $C_{20}H_{28}O_2$ | 13-cis-Retinoic acid, all-trans-retinoic acid |
| $C_{20}H_{30}O_2$ | cis-5, 8, 11, 14, 17-Eicosapentaenoic acid |
| $C_{20}H_{32}O_2$ | Arachadonic acid ($CH_3(CH_2)_4(CH=CHCH_2)_4(CH_2)_2COOH$) |
| $C_{20}H_{34}O_2$ | cis-8, 11, 14-Eicosatrienoic acid ($CH_3(CH_2)_7(CH=CHCH_2)_3(CH_2)_5COOH$) |
| $C_{20}H_{36}O_2$ | 11, 14-Eicosadienoic acid ($CH_3(CH_2)_7(CH=CHCH_2)_2(CH_2)_8COOH$) |
| $C_{20}H_{38}O_2$ | cis-11-Eicosenoic acid ($CH_3(CH_2)_7CH=CH(CH_2)_9COOH$) |
| $C_{20}H_{40}O_2$ | Eicosanoic acid, 2-octyldodecanoic acid |

Figure 23

INHIBITORS OF FATTY ACID AMIDE HYDROLASE

This application is a division of Ser. No. 09/536,842 filed Mar. 27, 2000 now U.S. Pat. No. 6,462,054.

GOVERNMENT RIGHTS

This invention was made, in part, with government support under Grants from NIH, viz., Grants No. CA42056 and MH58542. The U.S. government may have certain rights in the invention.

TECHNICAL FIELD

The present invention relates to inhibitors of fatty acid hydrolase. More particularly, the invention relates to inhibitors of fatty acid hydrolase employing a heterocyclic pharmacophore.

BACKGROUND

Fatty acid amide hydrolase (FAAH), referred to as oleamide hydrolase and anandamide amidohydrolase in early studies, is an integral membrane protein that degrades fatty acid primary amides and ethanolamides including oleamide and anandamide, as illustrated in FIG. 1 (M. P. Patricelli, et al., (1998) *Biochemistry* 37, 15177–15187. D. G. Deutsch, et al., (1993) *Biochem. Pharmacol.* 46, 791–796; F. Desarnaud, et al., (1995) *J. Biol. Chem.* 270, 6030–6035; C. J. Hillard, et al., (1995) *Biochim. Biophys. Acta* 1257, 249–256; N. Ueda, et al., (1995) *J. Biol. Chem.* 270, 23823–23827; R. L. Omeir, et al., (1995) *Life Sci.* 56, 1999–2005; S. Maurelli, et al., (1995) *FEBS Lett.* 377, 82–86; and M. Maccarrone, et al., (1998). *J. Biol. Chem.* 273, 32332–32339). The distribution of FAAH in the CNS suggests that it degrades neuromodulating fatty acid amides at their sites of action and is intimately involved in their regulation (E. A. Thomas, et al., (1997) *J. Neurosci. Res.* 50, 1047–1052). FAAH hydrolyzes a wide range of oleyl and arachidonyl amides, the CB1 agonist 2-arachidonylglycerol, the related 1-arachidonylglycerol and 1-oleylglycerol, and methyl arachidonate, illustrating a range of bioactive fatty acid amide or ester substrates. (W. Lang, et al., (1999) *J. Med. Chem.* 42, 896–902; S. K. Goparaju, et al., (1998) *FEBS Lett.* 442, 69–73; Y. Kurahashi, et al., (1997) *Biochem. Biophys. Res. Commun.* 237, 512–515; and T. Bisogno, et al., (1997) *Biochem. J.* 322, 671. Di Marzo, V., T. Bisogno, et al., (1998) *Biochem. J.* 331, 15–19). Although a range of fatty acid primary amides are hydrolyzed by the enzyme, FAAH appears to work most effectively on arachidonyl and oleyl substrates (B. F. Cravatt, et al., (1996) *Nature* 384, 83–87; and D. K. Giang, et al., (1997) *Proc. Natl. Acad. Sci. USA* 94, 2238–2242).

The important biological role of FAAH suggests a need for molecular regulators of its activity. However, only a select set of FAAH inhibitors have been disclosed. Amongst these is the potent endogenous inhibitor 2-octyl γ-bromoacetoacetate, which was discovered prior to FAAH and characterized as an endogenous sleep-inducing compound (M. P. Patricelli, et al., (1998) *Bioorg. Med. Chem. Lett.* 8, 613–618; and S. Torii, et al., (1973) *Psychopharmacologia* 29, 65–75). After the discovery of FAAH, elaborations of 2-octyl γ-bromoacetoacetate were developed and characterized as potent inhibitors of this enzyme. Moreover, subsequent inhibitors employ a fatty acid structure attached to pharmacophoric head group. The pharmacophoric head groups can generally be classified as either reversible or irreversible. Reversible inhibitors include electrophilic carbonyl moieties, e.g., trifluoromethyl ketones, α-halo ketones, α-keto esters and amides, and aldehydes. Irreversible inhibitors include sulfonyl fluorides and fluorophosphonates. (B. Koutek, et al., (1994) *J. Biol. Chem.* 269, 22937–22940; J. E. Patterson, et al., (1996) *J. Am. Chem. Soc.* 118, 5938–5945; D. L. Boger, et al., (1999) *Bioorg. Med. Chem. Lett.* 9, 167–172; D. G. Deutsch, et al., (1997) *Biochem. Pharmacol.* 53, 255–260. D. G. Deutsch, et al., (1997) *Biochem. Biophys. Res. Commun.* 231, 217–221; and L. De Petrocellis, et al., (1997) *Biochem. Biophys. Res. Commun.* 231, 82–88; and L. De Petrocellis, et al., (1998) In *Recent Advances Prostaglandin, Thromboxane, and Leukotriene Research*, Plenum Press: New York, 259–263).

SUMMARY OF INVENTION

One aspect of the invention is directed to an inhibitor of fatty acid amide hydrolase represented by the formula A—B—C. In this formula, A is an α-keto heterocyclic pharmacophore for inhibiting the fatty acid amide hydrolase; B is a chain for linking A and C, said chain having a linear skeleton of between 3 and 9 atoms selected from the group consisting of carbon, oxygen, sulfur, and nitrogen, the linear skeleton having a first end and a second end, the first end being covalently bonded to the α-keto group of A, with the following proviso: if the first end of said chain is an α-carbon with respect to the α-keto group of A, then the α-carbon is optionally mono- or bis-functionalized with substituents selected from the group consisting of fluoro, chloro, hydroxyl, alkoxy, trifluoromethyl, and alkyl; and C is an activity enhancer for enhancing the inhibition activity of said α-keto heterocyclic pharmacophore, said activity enhancer having at least one π-unsaturation situated within a π-bond containing radical selected from a group consisting of aryl, alkenyl, alkynyl, and ring structures having at least one unsaturation, with or without one or more heteroatoms, said activity enhancer being covalently bonded to the second end of the linear skeleton of B, the π-unsaturation within the π-bond containing radical being separated from the α-keto group of A by a sequence of no less than 4 and no more than 9 atoms bonded sequentially to one another, inclusive of said linear skeleton.

In a preferred embodiment, said α-keto heterocyclic pharmacophore is represented by the formula:

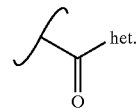

In the above formula, "het" is selected from the following group:

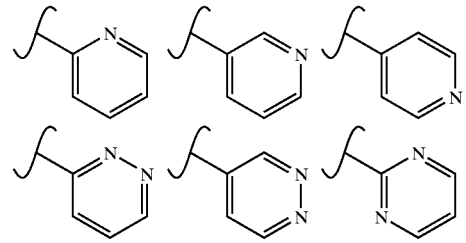

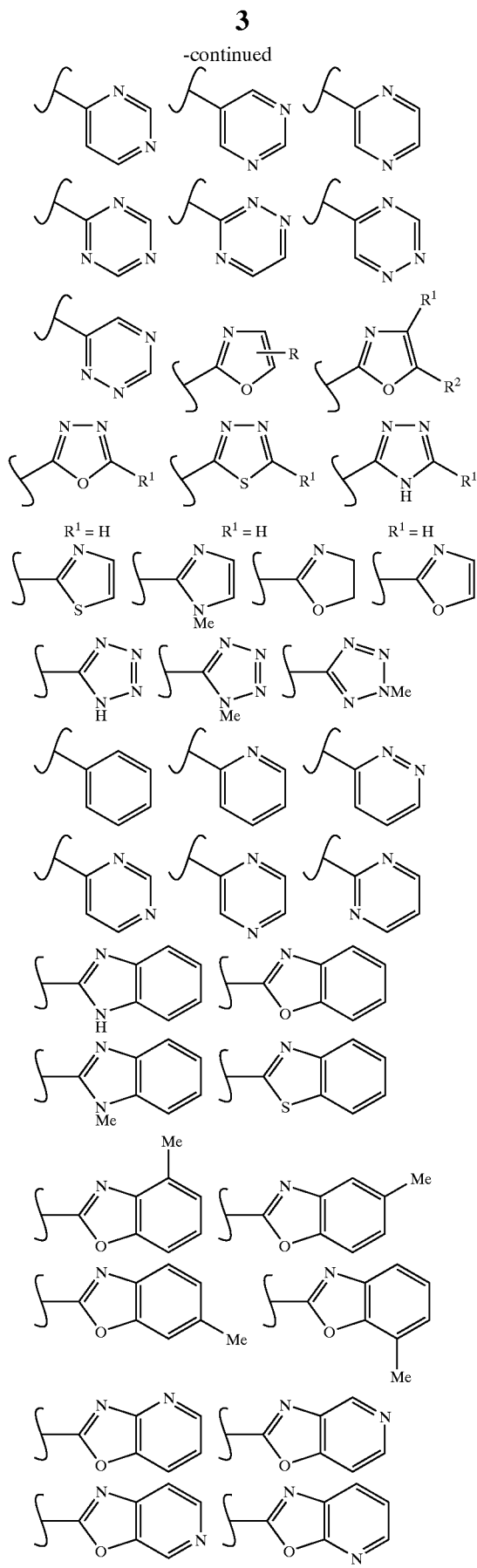
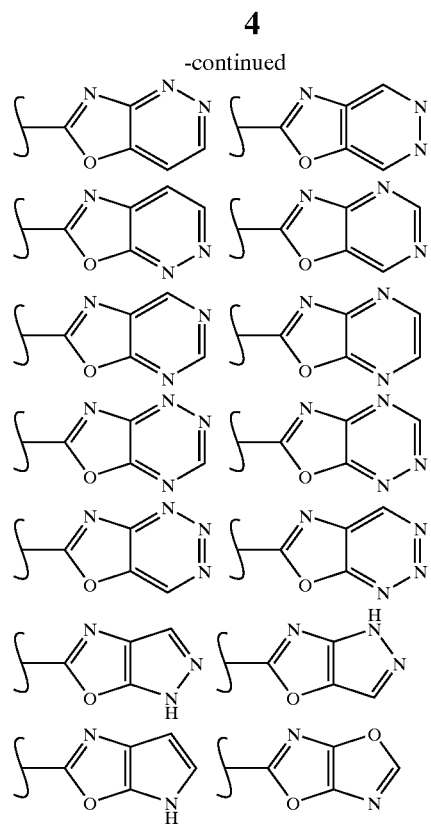
In a preferred mode of the above embodiment, "het" is selected from the following group:
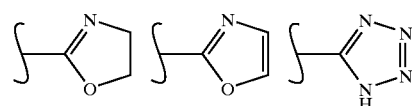
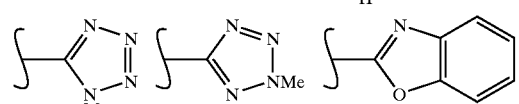
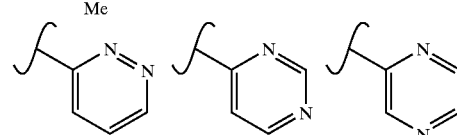
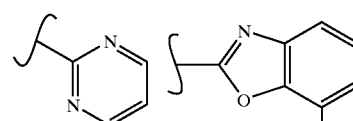
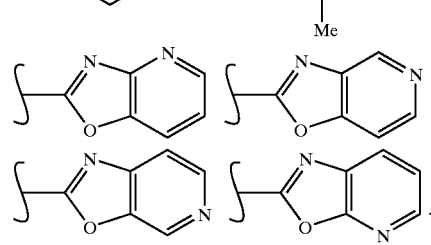
One group of inhibitors having a particularly high activity is represented by the following structure:

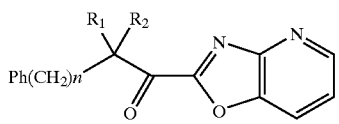

In the above structure, $R_1$ and $R_2$ are independently selected from the group consisting of hydrogen, fluoro, chloro, hydroxyl, alkoxy, trifluoromethyl, and alkyl; and "n" is an integer between 2 and 7.

Another aspect of the invention is directed to a process for inhibiting a fatty acid amide hydrolase. The process employs the step of contacting the fatty acid amide hydrolase with an inhibiting concentration of any of the above inhibitors represented above by the formula A—B—C.

Another aspect of the invention is directed to a process for enhancing SWS2 or REM sleep. The process employs the step of administering a therapeutically effective quantity to a patient of a fatty acid amide hydrolase inhibitors represented above by formula A—B—C.

BRIEF DESCRIPTION OF FIGURES

FIG. 3 is a table comparing the activity of α-keto heterocyclic inhibitors of FAAH with the corresponding trifluoromethyl ketone illustrating the enhancement of activity with the addition of basic nitrogen to the heterocyclic head group.

FIG. 4 is a table illustrating the steric effects of the methyl position of 4-, 5-, 6-, and 7-methylbenzoxazole head groups upon inhibitory activity with respect to FAAH catalysis and and employs this data to define the limits to depth and width of the FAAH active site.

FIG. 5 is a table illustrating the effects of nitrogen position within oxazolopyridine head groups with respect to inhibitory activity of FAAH catalysis.

FIG. 6 is a table illustrating the effects of unsaturations within the hydrocarbon tail of α-keto heterocyclic inhibitors with respect to inhibitory activity of FAAH catalysis. The data shows that for C18 $\Delta^{9,10}$ hydrocarbon tails, the effects of unsaturations upon inhibitory activity are as follows: Z (cis)>E (trans)>saturated.

FIG. 7 is a table illustrating the inhibitory activity of arachidonyl-based α-keto heterocyclic inhibitors with respect to FAAH catalysis. The data shows that arachidonyl-based α-keto heterocyclic inhibitors are more potent but much less stable than oleyl-based α-keto heterocyclic inhibitors.

FIG. 8 is a table illustrating the dependence of inhibitory activity upon the length of the fatty acid side chain of α-keto heterocyclic inhibitors and upon the length of the fatty acid side chain of α-keto heterocyclic inhibitors wherein the fatty acid side chain includes a terminal aromatic group.

FIG. 9 is a table comparing the inhibitory activity of α-hydroxy heterocycle inhibitors with that of α-keto heterocyclic inhibitors.

FIG. 10 is a table comparing the inhibitory activity of α-keto heterocyclic inhibitors against recombinant human FAAH and rat FAAH.

FIG. 11 illustrates how the ester is functionalized at the alpha position with fluorine, hydroxyl and trifluoromethyl groups. An asymmetric method for making a chiral alpha-fluoro ester is given, but one familiar with the art will know how to accomplish making the trifluoromethyl derivative in an asymmetric fashion. These methods assume that any functional groups that make up "R" are suitably protected.

FIG. 12 illustrates the methods by which chlorine, alpha-alkyl-alpha-hydroxyl, alpha-alkyl-alpha-Trifluoromethyl, and alpha-alkyl-alpha-fluoro groups may be added to an ester. Depending on what "R" is, some of these esters or the corresponding acids may be commercially available. A Mitsunobu reaction is done to obtain the alpha-chloro-compound from the corresponding alpha-hydroxy ester. An asymmetric hydroxylation of an enolate of an alpha-alkyl ester is accomplished by using an asymmetric oxaziridine (I). The last two products in this figure are obtained as racemates.

FIG. 15 lists the bicyclic heterocycles synthesized, the required methods of acylation, the starting material required, and literature references for synthesizing the desired heterocycles. Two methods of synthesizing the oxazolo[4,5-d]pyridazines are given as one may be superior for a given tail segment or functionality.

FIG. 16 is a continuation of FIG. 15 and the method of acylation was given in the specification.

FIG. 18 is a continuation of FIG. 17 and illustrates methods of acylation, starting materials, and literature references for 5,5 heteroaromatic compounds. The first compound may be obtained by the method given in the reference in column three. The starting materials are commercially available. The last type of heterocycle is a 5,5 heteroaromatic system that has seen much commercial application.

FIGS. 20–23 illustrate a partial list of commercially available hydrocarbon acids (from Aldrich (TM) catalog).

DETAILED DESCRIPTION

Figure 1:
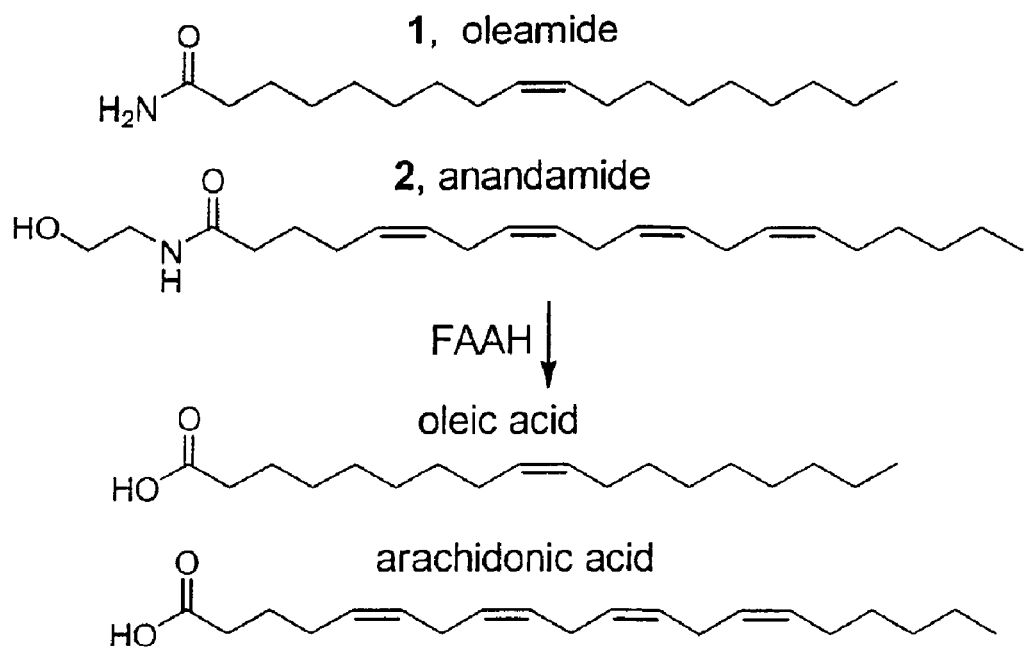
FIG. 1 illustrates the catalysis of the hydrolysis reaction by fatty acid amide hydrolase (FAAH) of oleamide and anandamide substrates and their conversion to oleic acid and arachidonic acid, respectively.

An unusually potent class of competitive inhibitors of FAAH was developed based on the additive, complementary binding interactions provided by the electrophilic carbonyl of an α-keto heterocycle and that of the heterocycles (e.g., oxazolopyridines) including a weakly basic nitrogen and other factors. The heterocycles are not spacially constrained and likely constitute an interaction with a mobile, active site residue intimately involved in the catalysis of the amide bond cleavage reaction. FAAH belongs to a new class of amidases that have not been extensively studied and appear to possess a distinct combination of active site residues involved in catalysis. Mutagenesis studies have characterized it as a possible serine-lysine type amidase which lacks a participating active site histidine (M. P. Patricelli, et al., (1999) *Biochemistry*, 38(43):14125–14130). It utilizes an active site serine nucleophile (Ser 241) and incorporates two additional active site serines (Ser 217 and 218) that enhance catalysis presumably by assisting proton transfer (M. P. Patricelli, et al., (1999) *Biochemistry* 38, 9804–9812). Key to its enhanced amide versus ester bond cleavage is its enlistment of a lysine (Lys 142) with a strongly perturbed pKa (7.8) as a base for Ser 241 deprotonation and which functions as a subsequent acid for protonation of the amine leaving group (M. P. Patricelli, et al., (1999) *Biochemistry*, 38(43):14125–14130). It is possible that the impact of the second, weakly basic nitrogen of the oxazolopyridines is derived from its hydrogen-bonding to one or more of these active sites residues and that the positioning of this residue is sufficiently flexible as to interact with a weakly basic nitrogen in a range of locations.

A number of well-defined relationships were observed in the development of the potent inhibitors. Several classes of oleyl α-keto heterocycles exhibit FAAH inhibition comparable to the corresponding α-keto ester and carboxamide. The more potent include 6-membered heterocycles incorporating a second, weakly basic nitrogen as well as benzoxazole. Substitution at any of the available sites on the α-keto benzoxazole inhibitor (C4–C7) eliminated activity defining limits to the depth and width of the FAAH active site Incorporation of an additional basic nitrogen into the benzoxazole skeleton providing the four isomeric oxazolopyridines (N4–N7), afforded exceptionally potent FAAH inhibitors 50–200 times more active than the benzoxazole and 840 times more active than the corresponding trifluoromethyl ketone.

Arachidonyl-based inhibitors were found to be 2–3 times more potent than the oleyl-based inhibitors consistent with the relative rates of FAAH hydrolysis of anandamide versus oleamide, but are sufficiently unstable as to preclude their effective use. The removal of the oleyl $\Delta^{9,10}$ cis double bond or the incorporation of a trans olefin reduced inhibitor potency consistent with prior observations (J. E. Patterson, et al., (1996) *J. Am. Chem. Soc.* 118, 5938–5945; and D. L. Boger, et al., (1999) *Bioorg. Med. Chem. Lett.* 9, 167–172). The inhibitor potency exhibited a smooth dependency on the fatty acid chain length, C18<C16<C14<C12–C8>C7>C6>C5>C2, exhibiting the maximum potency at C12–C8 which corresponds to the location of the oleyl $\Delta^{9,10}$ cis double bond and the arachidonyl $\Delta^{8,9}/\Delta^{11,12}$ double bonds. This appears to correspond to the location of a conformational bend, but not hairpin conformation, in the bound conformation identified with conformationally-restrained inhibitors (D. L. Boger, et al., (1999) *Bioorg. Med. Chem. Lett.* 9, 167–172). This indicates that the C1–C8 carbons of the inhibitors or substrates contribute substantially and incrementally to binding, and that the C14–C18/$C_{20}$ carbons may actually diminish binding. Incorporation of π-unsaturation into the medium length (C12–C8) inhibitors at the sites of oleyl or arachidonyl unsaturation further enhances the inhibitor potency and this may be accomplished with simple incorporation of a phenyl ring. The combination of these features: C8–C12 chain length, phenyl ring incorporation at the arachidonyl $\Delta^{8,9}$ and oleyl $\Delta^{9,10}$ location, and an α-keto N4-oxazolopyridine provides FAAH inhibitors with potencies that drop below $K_i$'s of 200 pM being $10^2$–$10^3$ times more potent than the corresponding trifluoromethyl ketones. With these potent inhibitors, the removal of the keto group reduces potency >$10^5$ times and its reduction to an alcohol reduces potency $10^3$ times. The α-hydroxy oxazolopyridines, while being $10^3$ times less potent than the corresponding ketones, exhibit effective FAAH binding and inhibition comparable to many of the initial α-keto heterocycles or related α-keto ester and carboxamide inhibitors. This indicates that there are complementary and significant independent active site interactions of the α-hydroxy group and the heterocycle. The interaction of the second basic nitrogen likely involves a mobile active site residue involved in the catalysis of amide bond cleavage and would be consistent with hydrogen-bonding to the active site nonnucleophile serines or catalytic lysine.

METHODS

Figure 2:
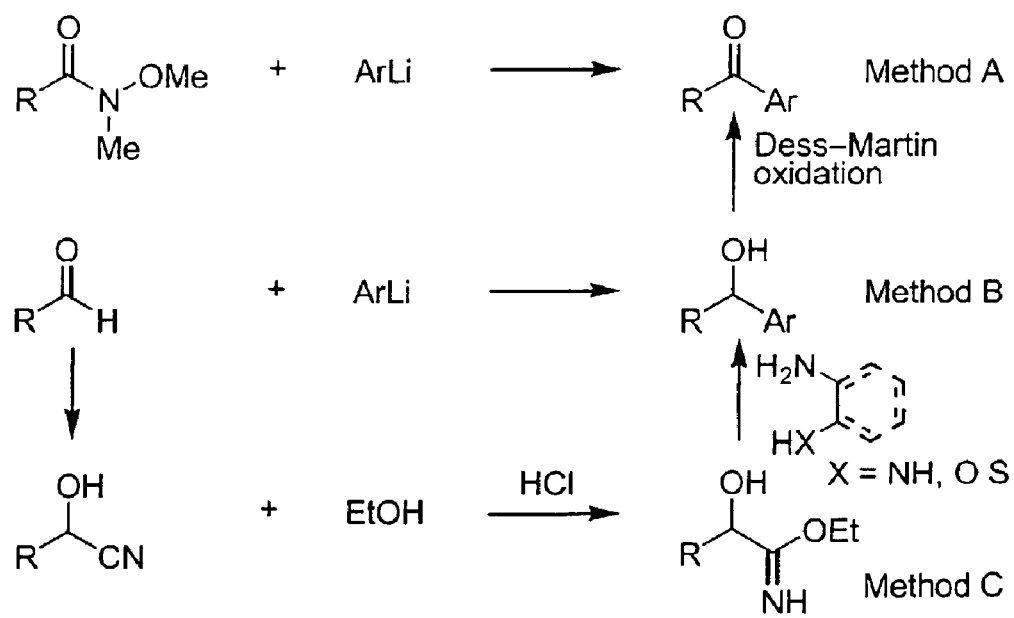
FIG. 2 schematically illustrates alternative routes for the synthesis of α-keto heterocyclic inhibitors of FAAH.
Figure 13:
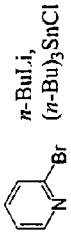
FIG. 13 illustrates various structures on the leftmost portion of the page which are just the heterocyclic portion of the alpha-keto heterocyclic FAAH inhibitor. The alpha-keto group, which includes the tail, is not shown. The method of acylation given is either one that is described in the specification or a palladium-catalyzed or an uncatalized acylation of a heteroaryl stannane with the desired acid chloride. The starting materials, along with their commercial sources are given in the second column. Those structures that are not commercially available have their synthesis described in the literature references listed in the third column. The remaining structures or compounds shown in the second column may be easily synthesized by methods known by a skilled practitioner in the art.
Figure 14:
FIG. 14 is a continuation of FIG. 13 and shows more monocyclic heterocycles and their methods of acylation, starting materials and literature references describing their syntheses. Where no method of acylation is given, it is contained within the references for the synthesis for that particular heterocycle. The use of an aryl stannane with the acid chloride under palladium-catalyzed cross-coupling reaction is assumed and a literature reference for this reaction was given in FIG. 13.
Figure 17:
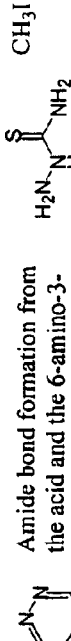
FIG. 17 is a continuation of FIG. 16 and illustrates methods of acylation, starting materials, and literature references for the remaining two 5,6 bicycloheteroaromatic compounds. Here, the method of acylation is more complex as it is stepwise. This is necessary because of the complex ring and lower stability of these compounds.
Figure 19:
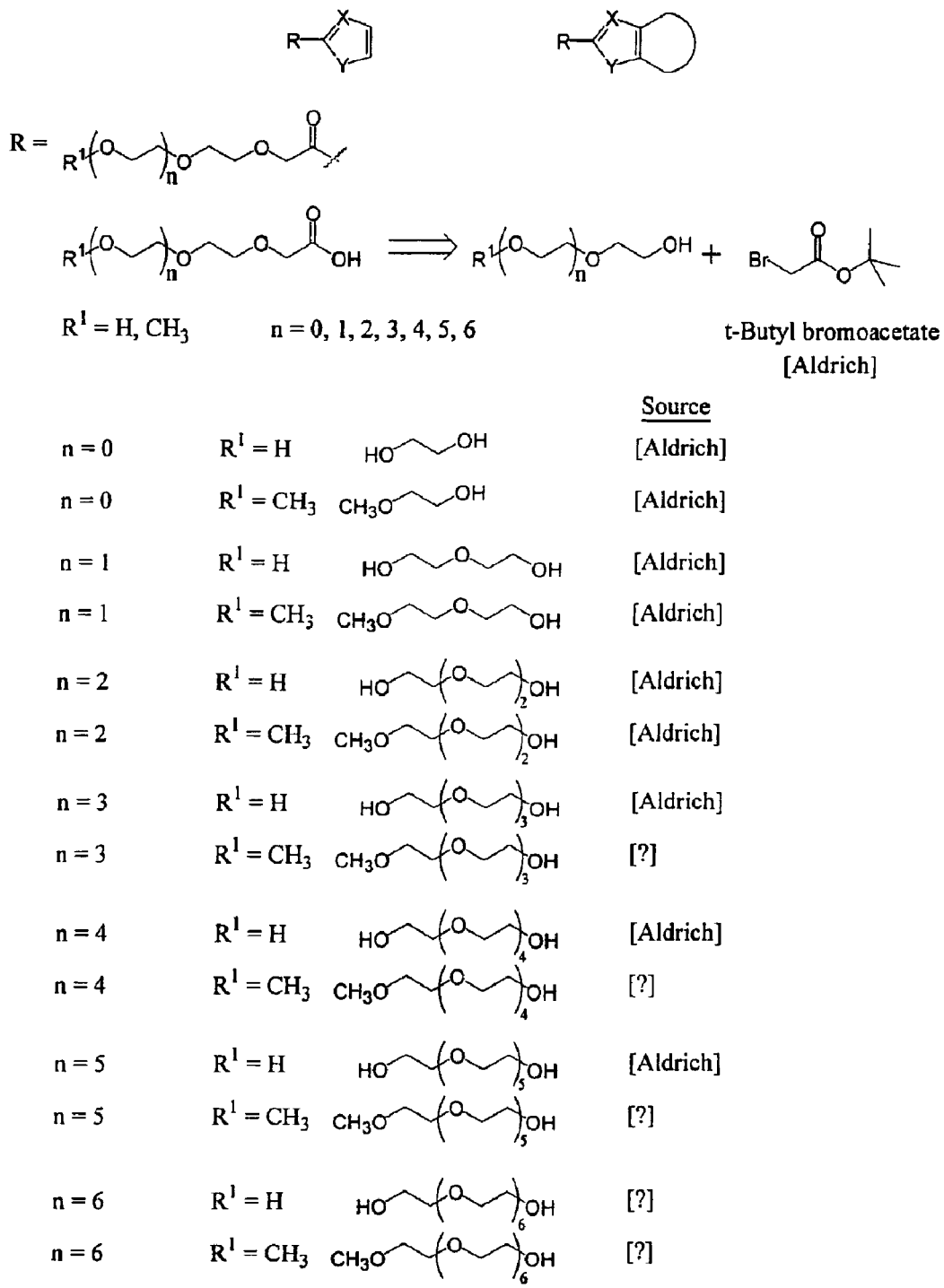
FIG. 19 illustrates in chart form oligoethylene glycol chains which are commercially available. The acylation of t-butyl bromoacetate is obtained as shown and and the hydrolysis of t-butyl esters is easily achieved in acidic solution to give the free acid.

Inhibitor Synthesis:

The α-keto heterocycles were prepared directly by addition of the heteroaryl lithium reagent to the Weinreb amide (Method A), or indirectly from the aldehyde proceeding through the α-hydroxy heterocycles followed by Dess-Martin oxidation via addition of the heteroaryl lithium reagent (Method B) or by cyanohydrin formation, acid-catalyzed conversion to the imidate (HCl—EtOH, $CHCl_3$), and condensation with a 2-aminoalcohol (oxazoline), 2-aminoaniline (benzimidazole), 2-aminophenol (benzoxazole), or o-amino-hydroxypyridine (oxazolopyridine) (Method C), FIG. 2. Full details of the inhibitor synthesis and characterization are provided in supplementary material.

Inhibition Studies:

All enzyme assays were performed at 20–23° C. using a solubilized liver plasma membrane extract containing FAAH in a reaction buffer of 125 mM Tris, 1 mM EDTA, 0.2% glycerol, 0.02% Triton X-100, 0.4 mM HEPES, pH 9.0 buffer (M. P. Patricelli, et al., (1998) *Bioorg. Med. Chem. Lett* 8, 613–618; and J. E. Patterson, et al., (1996) *J. Am. Chem. Soc.* 118, 5938–5945). The initial rates of hydrolysis were monitored by following the breakdown of $^{14}$C-oleamide to oleic acid as previously described (B. F. Cravatt, et al., (1995) *Science* 268, 1506–1509; and M. P. Patricelli, et al., (1998) *Bioorg. Med. Chem. Lett.* 8, 613–618). The inhibition was reversible, non time-dependent and linear least squares fits were used for all reaction progress curves and $R^2$ values were consistently >0.97. $IC_{50}$ values were determined from the inhibition observed at 3–5 different inhibitor concentrations (from three or more trials at each inhibitor concentration) using the formula $IC_{50}=[I]/[(K_0/K_1)-1]$, where $K_0$ is the control reaction rate without inhibitor and $K_1$ is the rate with inhibitor at concentration [I] (K. Conde-Frieboes, et al., (1996) *J. Am. Chem. Soc.* 118, 5519–5525). $K_1$ values were determined by the Dixon method α-intercepts of weighted linear fits of [I] versus 1/rate plots at constant substrate concentration, which were converted to $K_1$ values using the formula $K_1=-x_{int}/[1+[S]/$ $K_m$]). Previous work demonstrated the rat and human enzyme are very homologous (84%), exhibit near identical substrate specificities, and incorporate an identical amidase consensus sequence and SH3 binding domain suggesting the observations made with rat FAAH will be similar if not identical to those of human FAAH (B. F. Cravatt, et al., (1996) *Nature* 384, 83–87; and D. K. Giang, et al., (1997) *Proc. Natl. Acad. Sci. USA* 94, 2238–2242).

EXAMPLES

Nature of the Heterocycle:

A wide range of five- and six-membered monocyclic heterocycles and the three most prevalent bicyclic heterocycles (benzthiazole, benzimidazole, and benzoxazole) were incorporated into the oleyl α-keto heterocycles 8–24. The results of their examination are summarized in FIG. 3 along with the comparison data for the trifluoromethy ketone 3 and the related inhibitors 4–7 (J. E. Patterson, et al., (1996) *J. Am. Chem. Soc.* 118, 5938–5945). The inhibitors contain the oleyl chain possessing the 9-Z double bond and a carbonyl at the site of the oleamide carboxamide and adjacent to the electron-deficient heterocycle. Although, many of the inhibitors were more potent than oleyl aldehyde (4) and comparable to the α-keto ester 6 and carboxamide 7, only two, 14 and 10, matched the potency of the trifluoromethyl ketone 3. Many of the observations made by Edwards on the relative potencies of the α-keto heterocycles against elastase were also observed with FAAH. This includes the unique potency of the benzoxazole versus benzthiazole and benzimidazole, the more potent activity of the oxazole 10 versus the thiazole or imidazole, and the substantially more potent behavior of the 2-methyl versus 1-methyl tetrazoles 14 and 13. In contrast to the observations of Edwards and unique to the studies with FAAH, the oxazole 10 proved substantially more potent than the oxazoline 11, and the six-membered heterocycles containing two nitrogen atoms, one of which remains weakly basic (17–19 versus 20), were unusually potent exceeding the activity of the α-keto ester and carboxamide 7 and 8 and approaching that of trifluoromethyl ketone 3. Although there are many potential explanations for this behavior, one that was explored and proved consistent with subsequent observations is the enhancement of the inhibitor potency by incorporation of a weakly basic nitrogen.

Steric Requirements Surrounding the Benzoxazole:

The benzoxazole 23 was chosen for further examination since it provided the greatest opportunity for further functionalization. The 4-, 5-, 6-, and 7-methylbenzoxazoles were examined to define substitution sites available for functionalization without adversely affecting the inhibitor potency, FIG. 4. Substitution of any available position on the benzoxazole results in a greatly diminished (28) or complete loss of activity (25–27). This defines very precise limits to the size and depth of the FAAH active site which in turn has predictable implications on its substrate specificity or selectivity.

Oxazolopyridines: Incorporation of Nitrogen into the Benzoxazole:

Based on the observation that incorporation of an additional basic nitrogen into the heterocycles seemed to correlate with enhanced inhibitor potency, the four possible oxazolopyridines 29–32 were examined and found to be substantially more potent FAAH inhibitors, FIG. 5. The introduction of a nitrogen into the benzoxazole skeleton enhanced the potency 50–200 times providing inhibitors that are 10–50 times more potent than the trifluoromethyl ketone 3. Although N4 incorporation provided the most potent inhibitor 29, N5–N7 incorporation also provided effective inhibitors (N4>N6>N5>N7) and there is only a 4–5 fold difference in the most and least potent agent in the series. Although it is tempting to invoke an active site interaction that uniquely involves a dual interaction with N3 and N4, the comparable activity of 29–32 suggests the interaction of the second nitrogen is more flexible.

Since Edwards disclosure of α-keto heterocycles as effective protease inhibitors, a number of protease inhibitors have been disclosed based on analogous design principles (P. D. Edwards, et al., (1992) *J. Am. Chem. Soc.* 114, 1 854–1863; P. D. Edwards, et al., (1995) *J. Med. Chem.* 38, 76–85. Edwards, P. D., et al., (1995) *J. Med. Chem.* 38, 3972–3982; S. Tsutsumi, et al., (1994) *Bioorg. Med. Chem. Lett.* 4, 831–834. S. Tsutsumi, et al., (1994) *J. Med. Chem.* 37, 3492–3502; M. J. Costanzo, et al., (1996) *J. Med. Chem.* 39, 3039–3043; Y. Akiyama, et al., (1997) *Bioorg. Med. Chem. Lett.* 7, 533–538; S. Y. Tamura, et al., (1997) *Bioorg. Med. Chem. Lett.* 7, 1359–1364; W. Ogilvie, et al. (1997) *J. Med. Chem.* 40, 4113–4135; P. D. Boatman, et al., (1999) *J. Med. Chem.* 42, 1367–1375; and R. J. Cregge, et al., (1998) *J. Med. Chem.* 41, 2461–2480). The design principles developed by Edwards and others with regard to α-keto heterocyclic protease inhibitors may be employed in combination with the design principles disclosed herein with regard to α-keto heterocyclic FAAH inhibitors to achieve elevated potencies well beyond that achieved by simple introduction of the electrophilic carbonyl.

Impact of the Double Bond:

The importance of the oleyl double bond was examined with three of the initial potent inhibitors, FIG. 6. Identical to observations made with both the trifluoromethyl ketone and α-keto ester FAAH inhibitors, 29 and 17 containing the cis double bond were more potent than 33 and 35, respectively, containing the trans double bond which in turn were more potent than 34 and 36 in which the double bond was removed. Similarly, 23 was more potent than 37 and these results parallel those seen with the trifluoromethyl ketone inhibitors (J. E. Patterson, et al., (1996) *J. Am. Chem. Soc.* 118, 5938–5945; and D. L. Boger, et al., (1999) *Bioorg. Med. Chem. Lett.* 9, 167–172).

Arachidonyl-Based Inhibitors:

Since the two best substrates for FAAH are arachidonamide and oleamide, five of the potent α-keto heterocycles incorporated into the arachidonyl and compared to the analogous compounds having an oleyl skeleton, FIG. 7 (D. K. Giang, et al., (1997) *Proc. Natl. Acad. Sci. USA* 94, 2238–2242) In each instance, the inhibitors were unstable and decomposed fairly rapidly under typical working conditions. Several proved too unstable to purification to accurately assess their inhibitor potency and that of 40 could only be approximated (ca. 50% purity). Where this could be accurately assessed, the arachidonyl α-keto heterocycle inhibitors were 2–5 times more potent than the oleyl-based inhibitor. Despite this enhancement, which is consistent with the FAAH substrate preference for arachidonamide versus oleamide (rel. rate of hydrolysis 1:0.7), their instability precludes effective utility.

In studies with conformationally restricted trifluoromethyl ketone inhibitors, a well-defined trend favoring a bound bent, but not hairpin, conformation was observed and defined the shape characteristics of the active site (D. L. Boger, et al., (1999) *Bioorg. Med. Chem. Lett.* 9, 167–172). The enhanced potency of the arachidonyl-based inhibitors is likely to be related to this shape characteristic of the FAAH active site and their enhanced preference for adoption of the required bound conformation.

The Fatty Acid Chain:

Well-behaved trends were observed in exploring modifications in the fatty acid chain, FIG. 8. A very well-defined effect of the chain length was observed and the greatest potency was found with saturated straight chain lengths of C12–C8. This is a chain length that terminates at the location of the $\Delta^{9,10}$ double bond of oleamide and the $\Delta^{8,9}/\Delta^{11,12}$ double bond of arachidonamide and corresponds the location of the bend in the bound conformation identified in studies with trifluoromethyl ketone inhibitors (D. L. Boger, et al., (1999) *Bioorg Med. Chem. Lett.* 9, 167–172). Thus, the inhibitor potency progressively increased as the chain length was shortened from C18 to C12 ($K_1$, 11 (0.6 nM), leveled off at C12–C8 with subnanomolar $K_1$'s (0.57–0.73 nM), and subsequently diminished sharply as the chain length was further shortened from C18 to C2 ultimately providing inactive inhibitors ($K_1$, 0.7 (>100,000 nM). This indicates that each of the first C1–C8 carbons in the chain contribute significantly to inhibitor and substrate binding and that C10–C12 contribute nominally to binding. More importantly, it indicates that the terminal carbons of the longer C14–C18 inhibitors may actually diminish inhibitor binding affinity and may not be involved in substrate binding.

Incorporating unsaturation into the fatty acid chain increases inhibitor potency and its most effective incorporation examined proved to be that of a benzene ring, FIG. 8. This provided inhibitors with subnanomolar $K_1$'s with the most potent inhibitor 53 possessing a $K_1$ lower than 200 pM, below which an accurate $K_1$ could not be established in the present assay. This extraordinary potency was observed with the structurally simple inhibitors 51–53 readily amendable to further modification. These observations, like those of the straight chain inhibitors 42–50, are analogous to those made with a series of trifluoromethyl ketone inhibitors (D. L. Boger, et al., (1999) *Bioorg. Med. Chem. Lett.* 9, 167–172.). The distinction being that the α-keto oxazolopyridine inhibitors are $10^2$–$10^3$ times more potent than the corresponding trifluoromethyl ketones.

The Electrophilic Carbonyl:

Key to the design of the inhibitors was the electrophilic carbonyl which is required for potent enzyme inhibition. A select set of the α-hydroxy precursors to the initial inhibitors were examined and typically proved inactive as FAAH inhibitors, FIG. 9. Significantly, the α-hydroxy precursors 59 and 60 to the potent α-keto oxazolopyridines 29 and 44, respectively, retained significant FAAH inhibition with $K_1$'s of 1.8 and 1.2 μM, respectively. Although this is approximately $10^3$ times less potent than the corresponding keto derivative, they approximate the potency of the initial series of α-keto heterocycles and that of 4–7 (FIG. 3) including the oleyl aldehyde, α-keto ester, and α-keto carboxamide. This indicates that the pyridine nitrogen of the N4 oxazolopyridine, and presumably that of the N5–N7 oxazolopyridines, in conjunction with the α-hydroxy group contributes substantially to FAAH active site binding independent of the contributions of the electrophilic carbonyl. The corresponding agents 61 and 62 further lacking the α-hydroxy groups were inactive thereby losing an additional $10^2$ fold binding affinity with removal of the alcohol or $10^5$ fold binding affinities with respect to removal of the keto group.

Therapeutic Activity:

The in vivo properties of the inhibitors detailed herein and their action on the identified oleamide and anandamide potential sites of action are presented herein. A study with 17 with only 4 treated animals (10 mg/kg ip) versus controls revealed that within the first 4 h of administration, 17 decreased the time spent in wakefulness by 14% of the total time (20% reduction) and increased the time spent in SWS2 (10% increase of the total time, 45% increase) and REM sleep (4% increase of total time, 75% increase). Accordingly, the inhibitors disclosed herein are useful as inhibitors of FAAH and related amidases, and as a therapeutic agents with applications as sleep aids or analgesics which act by preserving endogenous levels of oleamide and anandamide.

Synthetic Protocols:

1-Oxo-1-(2-thiazolyl)-9(Z)-octadecene (8). Method A1:

A modification of the method of P. D. Edwards et al. was employed (Edwards, P. D., et al., (1995) *J. Med. Chem.* 38, 7685). A solution of thiazole (13.0 mg, 0.154 mmol, 1 equiv) in anhydrous THF (3.8 mL) at 30° C. was treated dropwise with n-BuLi (2.5 M in hexanes, 0.061 mL, 0.154 mmol, 1 equiv) under $N_2$ and the mixture was stirred for 30 min. A solution of the Weinreb amide of oleic acid (S1, N-methoxy-N-methyl-9(Z)-octadecenamide)$_3$ (50.0 mg, 0.154 mmol, 1 equiv) in anhydrous THF (1 mL) was added rapidly, and the mixture was stirred for 30 min at 30° C. Saturated aqueous NaCl (10 mL) was added and the mixture was extracted with $Et_2O$ (3 10 mL). The organic layers were dried ($Na_2SO_4$), filtered, and evaporated. Chromatography ($SiO_2$, 1.5 22 cm, 10–20% EtOAchexanes gradient elution) afforded 8 (20.0 mg, 37%) as a colorless oil.

1-(1-Methylimidazol-2-yl)-1-oxo-9(Z)-octadecene (9): This material was prepared in 66% yield from S1 and 1-methylimidazole using the procedure described as Method A1.

1-(1-Methylbenzimidazol-2-yl)-1-oxo-9(Z)-octadecene (22): This material was prepared in 62% yield from S1 and 1-methylbenzimidazole using the procedure described as Method A1.

1-(2-Benzothiazolyl)-1-oxo-9(Z)-octadecene (24): This material was prepared in 65% yield from S1 and benzothiazole using the procedure described as Method A1.

1-Oxo-1-(2-pyrazinyl)-9(Z)-octadecene (19). Method A2 (Ple, N., et al., (1995) *J. Org. Chem.* 60, 37813786): A solution of 2,2,6,6-tetramethylpiperidine (0.208 mL, 1.23 mmol, 4.0 equiv) in anhydrous THF (6.8 mL) at 30° C. was treated dropwise with n-BuLi (1.6 M in hexanes. 0.768 mL, 1.23 mmol, 4.0 equiv) under $N_2$. The reaction mixture was warmed to 0° C. and allowed to stir for 30 min. The reaction mixture was then cooled to 78° C., a solution of pyrazine (26.0 mg, 0.308 mmol, 1 equiv) in anhydrous THF (1 mL) was added, and then a solution of S1 (100.0 mg, 0.308 mmol, 1 equiv) in anhydrous THF (0.5 mL) was added. After the mixture was stirred for 1 h at 78° C., a mixture of 12 N HCl/THF/EtOH (1:4.5:4.5) (20 mL) was added and the reaction mixture was slowly warmed to 25° C. Saturated aqueous $NaHCO_3$ (20 mL) was added and the mixture was extracted with $CH_2Cl_2$ (3 20 mL). The organic layers were dried ($Na_2SO_4$), filtered, and evaporated. Chromatography ($SiO_2$, 1.5 25 cm, 10–40% EtOAchexanes gradient elution) afforded 19 (13.0 mg, 12%) as a yellow oil.

1-Oxo-1-(2-pyridyl)-9(Z)-octadecene (16): This material was prepared in 76% yield from S1 and 2-bromopyridine using the procedure described as Method A2.

1-Oxo-1-(3-pyridazinyl)-9(Z)-octadecene (17): This material was prepared in 11% yield from S1 and pyridazine using the procedure described as Method A2. 17; mp 4042° C.

1-Oxo-1-phenyl-9(Z)-octadecene (15). Method A3: A solution of S1 (111.1 mg, 0.341 mmol, 1 equiv) in anhydrous THF (1 mL) at 0° C. was treated dropwise with phenylmagnesium bromide (1.0 M in THF, 0.68 mL, 0.680 mmol, 2 equiv) under $N_2$ and stirred for 1 h. Cold-water (1 mL) was added slowly and the resulting mixture was extracted with EtOAc (3 15 mL) and washed with $H_2O$ (20 mL). The organic layers were dried ($Na_2SO_4$), filtered, and evaporated.

Chromatography ($SiO_2$, 1.5 20 cm, 2% EtOAchexanes) afforded 15 (97.4 mg, 83%) as a colorless oil.

N-Methoxy-N-methyl-9(E)-octadecenamide (S2). A solution of elaidic acid (1.0 g, 3.54 mmol, 1 equiv) in anhydrous $CH_2Cl_2$ (17 mL) at 0° C. was treated dropwise with oxalyl chloride (2 M in $CH_2Cl_2$, 5.25 mL, 10.5 mmol, 2.97 equiv) under $N_2$. The reaction mixture was allowed to warm to 25° C. and stirred for 3 h. The solvent was evaporated to afford the crude carboxylic acid chloride. Excess N,O-dimethylhydroxylamine in EtOAc (the hydrochloride salt was extracted into EtOAc from a 50% aqueous NaOH solution before use) was added slowly to the ice-cold crude material. The reaction mixture was stirred for 1 h, quenched with the addition of $H_2O$ (20 mL), and extracted with EtOAc (3 15 mL). The organic layers were dried ($Na_2SO_4$), filtered, and evaporated. Chromatography ($SiO_2$, 2.5 20 cm, 30–60% EtOAchexanes gradient elution) afforded S2 (0.96 g, 83%) as a colorless oil.

1-Oxo-1-(3-pyridazinyl)-9(E)-octadecene (35): This material was prepared in 40% yield from S2 and pyridazine using the procedure described as Method A2.

N-Methoxy-N-methyl-octadecanamide (S3): This material was prepared in 99% yield from octadecanoic acid using the procedure described above for S2. S3; mp 3234° C.

1-Oxo-1-(3-pyridazine)octadecane (36): This material was prepared in 12% yield from S3 and pyridazine using the procedure described as Method A2. 36; mp 8385° C.

N-Methoxy-N-methyl-arachidonamide (S4): This material was prepared in 96% yield from arachidonic acid using the procedure described above for compound S2.

1-(3-Pyridazinyl)arachidonaldehyde (41): This material was prepared in 32% yield from S4 and pyridazine using the procedure described as Method A2.

1-Oxo-1-(4-pyrimidyl)-9(Z)-ocadecene (18). Method B:

1-Hydroxy-1-(4-pyrimidyl)-9(Z)-octadecene: This material was prepared in 9% yield from the aldehyde and pyrimidine using the procedure described as Method A2.

1-Oxo-1-(4-pyrimidyl)-9(Z)-octadecene (18): A solution of the alcohol (22.0 mg, 0.0635 mmol, 1 equiv) in anhydrous $CH_2Cl_2$ (7 mL) was treated with DessMartin's periodinane (46.0 mg, 0.109 mmol, 1.71 equiv). The reaction mixture was stirred at 25 C for 3 h. A mixture of 10% aqueous $Na_2S_2O_3$/saturated aqueous $NaHCO_3$ (1:1) (20 mL) was added and the reaction mixture was stirred for 10 min. The reaction mixture was extracted with $CH_2Cl_2$ (3 15 mL). The organic layers were dried ($Na_2SO_4$), filtered, and evaporated. Chromatography ($SiO_2$, 1.5 20 cm, 1% $MeOHCH_2Cl_2$) afforded 18 (17.3 mg, 79%) as a colorless oil.

1-Hydroxy-1-(1-benzyloxymethyl-1H-tetrazol-5-yl)-9(Z)-octadecene: This material was prepared in 57% yield from oleyl aldehyde and 1-benzyloxymethyl-1H-tetrazole using the procedure described as Method A1.

1-Hydroxy-1-(1H-tetrazol-5-yl)-9(Z)-octadecene: A solution of the addition product above (59.1 mg, 0.129 mmol, 1 equiv) in 1,4-dioxane (3 mL) at 25° C. was treated with 12 N HCl (3 ml, 36 mmol, 280 equiv) and stirred for 1 h. $H_2O$ (15 mL) was added to the reaction mixture. The mixture was extracted with EtOAc (3 20 mL) and washed with saturated aqueous NaCl (20 mL). The organic layers were dried ($Na_2SO_4$), filtered, and evaporated. Chromatography ($SiO_2$, 1.5 20 cm, 05% MeOHEtOAc gradient elution) afforded the product (40.5 mg, 93%) as a white solid; mp 7576° C.

1-Hydroxy-1-(2-methyl-2H-tetrazol-5-yl)-9(Z)-octadecene and 1-Hydroxy-1-(1-methyl-1H-tetrazol-5-yl)-9 (Z)-octadecene: A suspension of the precursor alcohol (10.0 mg, 0.0297 mmol, 1 equiv) in anhydrous DMF (0.5 mL), MeI (6.0 uL, 0.0964 mmol, 3.25 equiv), and $K_2CO_3$ (8.3 mg, 0.060 mmol, 2.02 equiv) was stirred for 30 min at 0° C. The reaction mixture was warmed to 25° C. and stirred for 16 h. $H_2O$ (10 mL) was added to the reaction mixture. The mixture was extracted with $Et_2O$ (3 15 mL) and washed with $H_2O$ (10 mL). The organic layers were dried ($Na_2SO_4$), filtered, and evaporated. Chromatography ($SiO_2$, 1.5 17 cm, 2% $MeOHCH_2Cl_2$) to afford the alcohol precursors to 14 (1.8 mg, 17%) and 13 (2.7 mg, 26%) and their mixture (4.9 mg, 47%) as colorless oils.

1-(2-Methyl-2H-tetrazol-5-yl)-1-oxo-9(Z)-octadecene (14): This material was prepared in 67% yield from the alcohol using the procedure described for 18.

1-(1-Methyl-1H-tetrazol-5-yl)-1-oxo-9(Z)-octadecene (13): This material was prepared in 34% yield from the alcohol using the procedure described for 18.

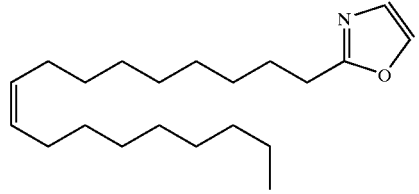

1-Oxazolo-1-oxo-9(Z)-octadecene (10): A solution of oxazole (39 mg, 0.56 mmol, 1.0 equiv) in anhydrous THF (6.0 mL) at −78° C. was treated dropwise with n-BuLi (2.5 M in hexanes, 0.340 mL, 0.85 mmol, 1.4 equiv) under $N_2$ and the resulting solution was stirred at −78° C. for 20 min. $ZnCl_2$ (0.5 M in THF, 2.260 mL, 1.13 mmol, 2.0 equiv) was added to the mixture, and the mixture was warmed to 0° C. The mixture was stirred at 0° C. for 45 min, before CuI (107 mg, 0.56 mmol, 1.0 equiv) was added to the mixture. The mixture was stirred at 0° C. for 10 min, before a solution of 9(Z)-octadecenyl chloride (prepared from 320 mg of oleic acid and 432 mg of oxalyl chloride, 1.13 mmol, 2.0 equiv) in anhydrous THF (11 mL) was added dropwise and the mixture was stirred at 0° C. for an additional 1 h. The reaction mixture was diluted with EtOAc (30 mL) and washed with 1:1 $NH_4OH$-water (20 mL), $H_2O$ (20 mL) and saturated aqueous Naa (20 mL), successively. The organic layer was dried ($Na_2SO_4$), filtered, and evaporated. Column chromatography ($SiO_2$, 2.4 (10 cm, 5–10% $Et_2O$-hexanes gradient elution) afforded 1-oxazolo-1-oxo-9(Z)-octadecene (49.1 mg, 0.15 mmol, 26% yield) as a pale yellow oil.

The reaction conditions are reported to provide C-2 regioselective acylation of oxazole and its derivatives (Ham, N. K., et al., (1995) *Tetrahedron Lett.* 36, 9453–9456). The chemical shifts of the oxazole protons of the product ($^1$H NMR) confirmed that it is the desired C-2 acylated oxazole, compared with those of potential regioisomers (Hodges, J. C., et al., (1991) *J. Org. Chem.* 56, 449452; and Edwards, P. D., et al., (1995) *J. Med. Chem.* 38, 76–85).

1-(2-Oxazolinyl)-1-oxo-9(Z)-octadecene (11). Method C1: A solution of oleyl aldehyde (1.14 g, 4.27 mmol, 1 equiv) in THF (15 mL) and $H_2O$ (16.5 mL) was treated with KCN (2.81 g, 43.2 mmol, 10.1 eq). The reaction mixture was stirred at 25° C. for 72 h. $H_2O$ (20 mL) and $Et_2O$ (20 mL) were added to the reaction mixture. The mixture was extracted with Et$_2$O (3 20 mL) and washed with saturated aqueous NaHCO$_3$ (20 mL) and saturated aqueous NaCl (20 mL). The organic layers were dried (Na$_2$SO$_4$), filtered, and evaporated to afford the cyanohydrin (1.26 g, quant.) as an oil which was used without further purification.

A solution of anhydrous EtOH (0.76 mL, 12.9 mmol, 20.0 equiv) in CHCl$_3$ (1 mL) at 0 C was treated with acetyl chloride (0.74 mL, 10.4 mmol, 16.1 equiv) followed by a solution of the cyanohydrin (189.6 mg, 0.646 mmol, 1 equiv) in CHCl$_3$ (2 mL). The reaction mixture was allowed to warm to 25 C and stirred for 13 h. The solvent was evaporated to afford the imidate as a white solid which was used without further purification.

A solution of the imidate in anhydrous CH$_2$Cl$_2$ (3 mL) was treated with ethanolamine (78 μL, 1.29 mmol, 2.0 equiv) and triethylamine (180 μL, 1.29 mmol, 2.0 equiv). The reaction mixture was stirred at 25 C for 22 h. Et$_2$O (20 mL) and H$_2$O (20 mL) were added and the reaction mixture was extracted with Et$_2$O (3 20 mL), and washed with saturated aqueous NaCl (20 mL). The organic layers were dried (Na$_2$SO$_4$), filtered, and evaporated. Chromatography (SiO$_2$, 1.5 18 cm, 7580% EtOAchexanes gradient elution) afforded the alcohol (72 mg) as a colorless oil.

A solution of the alcohol (72 mg) in anhydrous CH$_2$Cl$_2$ (5 mL) was treated with DessMartin's periodinane (152.3 mg, 0.36 mmol). The reaction mixture was stirred at 25 C for 70 min. Et$_2$O (20 mL) and saturated aqueous Na$_2$S$_2$O$_3$/saturated aqueous NaHCO$_3$ (1:1) (20 mL) were added and reaction mixture was stirred for 10 min. The mixture was extracted with Et$_2$O/EtOAc (2:1) (3 30 mL) and washed with saturated aqueous NaHCO$_3$ (20 mL) and saturated aqueous NaCl (20 mL). The organic layers were dried (Na$_2$SO$_4$), filtered, and evaporated. Chromatography (SiO$_2$, 1.5 18 cm, CH$_2$Cl$_2$) afforded 11 (40.7 mg, overall 18%) as a colorless oil.

1-(2-Benzoxazolyl)-1-hydroxy-9(Z)-octadecene (57). Method C2: A modification of the method of P. D. Edwards et al. was employed (Edwards, P. D., et al., (1995) *J. Med. Chem.* 38, 7685). A solution of anhydrous EtOH (0.42 mL, 7.16 mmol, 20.4 equiv) in CHCl$_3$ (1 mL) at 0 C was treated with acetyl chloride (0.40 mL, 5.63 mmol, 16.0 equiv) followed by a solution of oleyl aldehyde cyanohydrin (103.0 mg, 0.351 mmol, 1 equiv) in CHCl$_3$ (1 mL). The reaction mixture was allowed to warm to 25 C and stirred for 16 h. The solvent was evaporated to afford the imidate as a white solid which was used without further purification. A solution of the imidate in EtOH (2 mL) was treated with 2-aminophenol (39.4 mg, 0.36 mmol, 1.03 equiv). The reaction mixture was heated to 60 C for 4.5 h. Et$_2$O (10 mL) and 1 N aqueous NaOH (10 mL) were added and the reaction mixture was extracted with EtOAc/Et$_2$O (2:1) (3 20 mL), and washed with saturated aqueous NaCl (20 mL). The organic layers were dried (Na$_2$SO$_4$), filtered, and evaporated. Chromatography (SiO$_2$, 1.5 20 cm, CH$_2$Cl$_2$) afforded the product alcohol 57 (69.4 mg, 51%) as a pale yellow oil.

1-Hydroxy-1-(4-methylbenzoxazol-2-yl)-9(Z)-octadecene: This material was prepared in 47% yield from oleyl aldehyde cyanohydrin and 2-amino-m-cresol using Method C2.

1-Hydroxy-1-(5-methylbenzoxazol-2-yl)-9(2)-octadecene: This material was prepared in 79% yield from oleyl aldehyde cyanohydrin and 2-amino-p-cresol using Method C2.

1-Hydroxy-1-(6-methylbenzoxazol-2-yl)-9(Z)-octadecene: This material was prepared in 59% yield from oleyl aldehyde cyanohydrin and 6-amino-m-cresol using Method C2.

1-Hydroxy-1-(7-methylbenzoxazol-2-yl)-9(Z)-octadecene: This material was prepared in 53% yield from oleyl aldehyde cyanohydrin and 6-amino-o-cresol (Bisarya, S. C., et al., (1993) *Synth. Commun.* 23, 1125–1137) using Method C2.

1-(2-Benzoxazolyl)-1-oxo-9(Z)-octadecene (23): This material was prepared in 67% yield from the alcohol using the procedure described for 18.

1-(4-Methylbenzoxazol-2-yl)-1-oxo-9(Z)-octadecene (25): This material was prepared in 81% yield from the alcohol using the procedure described for 18.

1-(5-Methylbenzoxazol-2-yl)-1-oxo-9(Z)-octadecene (26): This material was prepared in 35% yield from the alcohol using the procedure described for 18.

1-(6-Methylbenzoxazol-2-yl)-1-oxo-9(Z)-octadecene (27): This material was prepared in 66% yield from the alcohol using the procedure described for 18.

1-(7-Methylbenzoxazol-2-yl)-1-oxo-9(Z)-octadecene (28): This material was prepared in 74% yield from the alcohol using the procedure described for 18.

1-(2-Benzimidazolyl)-1-hydroxy-9(Z)-octadecene (58): This material was prepared in 54% yield from oleyl aldehyde cyanohdrin and 1,2-phenylenediamine using the procedure described as Method C2. 58; mp 109–110 C.

1-(2-Benzimidazolyl)-1-oxo-9(Z)-octadecene (21): This material was prepared in 73% yield from the alcohol using the procedure described for 18.

1-Hydroxy-1-(oxazolo[4,5-b]pyridin-2-yl)-9(Z)-octadecene (59). Method C3: A solution of anhydrous EtOH (0.52 mL, 8.86 mmol, 20.6 equiv) in CHCl$_3$ (1 mL) at 0 C was treated with acetyl chloride (0.50 mL, 7.03 mmol, 16.4 equiv) followed by a solution of oleyl aldehyde cyanohydrin (126.3 mg, 0.430 mmol, 1 equiv) in CHCl$_3$ (1.5 mL). The reaction mixture was allowed to warn to 25 C and stirred for 13 h. The solvent was evaporated to afford the imidate as a white solid which was used without further purification.

A solution of the imidate in dry EtOCH$_2$CH$_2$OH (1.5 mL) was treated with 2-amino-3-hydroxypyridine (48.0 mg, 0.436 mmol, 1.01 equiv). The reaction mixture was heated at 130 C for 6 h. The reaction mixture was evaporated and the residue was dissolved in EtOAc/Et$_2$O (2:1) (50 mL) and 1 N aqueous NaOH (10 mL), and washed with saturated aqueous NaCl (20 mL). The organic layers were dried (Na$_2$SO$_4$), filtered, and evaporated. Chromatography (SiO$_2$, 1.5 18 cm, 3% MeOHCH$_2$Cl$_2$ and then SiO$_2$, 1.5 18 cm, 66% EtOAchexanes) afforded the product alcohol 59 (27.3 mg, 16%) as a pale brown oil.

1-Hydroxy-1-(oxazolo[4,5-c]pyridin-2-yl)-9(Z)-octadecene: This material was prepared in 0.7% yield from oleyl aldehyde cyanohydrin and 3-amino-4-hydroxypyridine using Method C2.

1-Hydroxy-1-(oxazolo[4,5-d]pyridin-2-yl)-9(Z)-octadecene: This material was prepared in 1.7% yield from oleyl aldehyde cyanohydrin and 4-amino-3-hydroxypyridine using Method C3.

1-Hydroxy-1-(oxazolo[4,5-e]pyridin-2-yl)-9(Z)-octadecene: This material was prepared in 2% yield from oleyl aldehyde cyanohydrin and 3-amino-2-hydroxypyridine using Method C2.

1-(Oxazolo[4,5-b]pyridin-2-yl)-1-oxo-9(Z)-octadecene (29): This material was prepared in 76% yield from the alcohol using the procedure described for 18.

1-(Oxazolo[4,5-c]pyridin-2-yl)-1-oxo-9(Z)-octadecene (30): This material was prepared in 87% yield from the alcohol using the procedure described for 18. 1-(Oxazolo[4,5-d]pyridin-2-yl)-1-oxo-9(Z)-octadecene (31): This material was prepared in 28% yield from the alcohol using the procedure described for 18.

1-(Oxazolo[4,5-e]pyridin-2-yl)-1-oxo-9(Z)-octadecene (32): This material was prepared in 36% yield from the alcohol using the procedure described for 18.

1-(2-Benzoxazolyl)-1-oxo-octadecane (37): A solution of 23 (5.2 mg, 0.0136 mmol) in MeOH (0.5 mL) was combined with 10% PdC (2.2 mg) under $N_2$. The atmosphere was purged with $H_2$ and the reaction mixture was stirred at 25 C for 10 min. The reaction mixture was filtered and evaporated. Chromatography ($SiO_2$, 1.5 10 cm, 50% $CH_2Cl_2$ hexanes) afforded 37 (2.4 mg, 46%) as a white solid; mp 71–72 C.

1-(Oxazolo[4,5-b]pyridin-2-yl)-1-oxo-octadecane (34): This material was prepared in 72% yield from 29 using the procedure described for 37.

1-Hydroxy-1-(oxazolo[4,5-b]pyridin-2-yl)-9(E)-octadecene: This material was prepared in 15% overall yield from 9(E)-octadecenal and 2-amino-3-hydroxypyridine using Method C3.

1-(Oxazolo[4,5-b]pyridin-2-yl)-1-oxo-9(E)-octadecene (33): This material was prepared in 60% yield from the alcohol using the procedure described for 18. 33; mp 49–51° C.

1-Hydroxy-1-(oxazolo[4,5-b]pyridin-2-yl)-5(Z),8(Z),11(Z),14(Z)-cicosatetraene: This material was prepared in 10% yield from arachidonyl aldehyde and 2-amino-3-hydroxypyridine using Method C3.

1-(Oxazolo[4,5-b]pyridin-2-yl)arachidonaldehyde (38): This material was prepared in 31% yield from the alcohol using the procedure described for 18.

1-(Oxazolo[4,5-c]pyridin-2-yl)arachidonaldehyde (39): 1-Hydroxy-1-(oxazolo[4,5-c]pyridin-2-yl)-5(Z),8(Z), 11(Z), 14(Z)-eicosatetraene was prepared from arachidonyl aldehyde and 3-amino-4-hydroxypyridine using method C3. This unstable alcohol was immediately oxidized using the procedure described for 18 to give 39.

1-(Oxazolo[4,5-d]pyridin-2-yl) arachidonaldehyde (40): 1-Hydroxy-1-(oxazolo[4,5-d]pyridin-2-yl)-5(Z),8(Z),11(Z),14(Z)-eicosatetraene was prepared from arachidonyl aldehyde and 4-amino-3-hydroxypyridine using method C3. This unstable alcohol was immediately oxidized using the procedure described for 18 to give 40.

1-Hydroxy-1-(oxazolo[4,5-b]pyridin-2-yl)hexadecane. Method C4: A solution of hexadecanal (160.0 mg, 0.666 mmol, 1 equiv) in THF (5.7 mL) and $H_2O$ (6.2 mL) was treated with KCN (446.1 mg, 6.85 mmol, 10.3 equiv). The reaction mixture was stirred at 25° C. for 70 h. $H_2O$ (20 m/L) and $Et_2O$ (20 mL) were added to the reaction mixture. The mixture was extracted with $Et_2O$ (3 20 mL) and washed with saturated aqueous $NaHCO_3$ (20 mL) and saturated aqueous NaCl (20 mL). The extracts were dried ($Na_2SO_4$), filtered, and evaporated to afford the cyanohydrin (162.0 mg, 91%) as a white solid which was used without further purification.

A solution of anhydrous EtOH (0.72 mL, 12.1 mmol, 20.0 equiv) in $CHCl_3$ (1.5 mL) at 0 C was treated with acetyl chloride (0.69 mL, 9.70 mmol, 16.0 equiv) followed by a solution of the cyanohydrin (162.0 mg, 0.606 mmol, 1 equiv) in $CHCl_3$ (3 mL). The reaction mixture was allowed to warm to 25 C and stirred for 20.5 h. The solvent was evaporated to afford the imidate as a white solid which was used without further purification.

A solution of the imidate in dry 2-ethoxyethanol (2.5 mL) was treated with 2-amino-3-hydroxypyridine (66.6 mg, 0.605 mmol, 1.0 equiv). The reaction mixture was heated to 125 C for 6.5 h. The reaction mixture was evaporated and the residue was dissolved in $EtOAc/Et_2O$ (2:1) (60 mL) and 1 N aqueous NaOH (10 mL), and washed with saturated aqueous NaCl (20 mL). The organic layers were dried ($Na_2SO_4$), filtered, and evaporated. Chromatography ($SiO_2$, 1.5 22 cm, 3% $MeOHCH_2Cl_2$ and then $SiO_2$, 1.5 20 cm, 66% EtOAchexanes) afforded the alcohol (24.7 mg, 11%) as a pale brown solid; mp 59–61° C.

1-Hydroxy-1-(oxazolo[4,5-b]pyridin-2-yl)ethane: This material was prepared acetaldehyde using the Method C4.

1-Hydroxy-1-(oxazolo[4,5-b]pyridin-2-yl)pentane: This material was prepared from pentanal using Method C4.

1-Hydroxy-1-(oxazolo[4,5-b]pyridin-2-yl)hexane: This material was prepared from hexanal using Method C4.

1-Hydroxy-1-(oxazolo[4,5-b]pyridin-2-yl)heptane: This material was prepared from heptanal using Method C4.

1-Hydroxy-1-oxazolo[4,5-b]pyridin-2-yl)octane: This material was prepared from octanal using Method C4.

1-Hydroxy-1-(oxazolo[4,5-b]pyridin-2-yl)decane: This material was prepared from decanal using Method C4.

1-Hydroxy-1-(oxazolo[4,5-b]pyridin-2-yl)dodecane (60): This material was prepared from dodecanal using Method C4.

1-Hydroxy-1-(oxazolo[4,5-b]pyridin-2-yl)tetradecane: This material was prepared from tetradecanal using Method C4: mp 52–54° C.

1-Hydroxy-1-(oxazolo[4,5-b]pyridin-2-yl)-6-phenylhexane: This material was prepared from 6-phenylhexanal using Method C4.

1-Hydroxy-1-(oxazolo[4,5-b]pyridin-2-yl)-7-phenylheptane: This material was prepared from 7-phenylheptanal using Method C4.

1-Hydroxy-1-(oxazolo[4,5-b]pyridin-2-yl)-8-phenyloctane: This material was prepared from 8-phenyloctanal using Method C4.

1-(Oxazolo[4,5-b]pyridin-2-yl)-1-oxo-hexadecane (42): This material was prepared in 65% yield from the alcohol using the procedure described for 18. 42; mp 77–78° C.

1-(Oxazolo[4,5-b]pyridin-2-yl)-1-oxo-ethane (50): This material was prepared in 75% yield from the alcohol using the procedure described for 18. 50; mp 103–105° C.

1-(Oxazolo[4,5-b]pyridin-2-yl)-1-oxo-pentane (49): This material was prepared in 64% yield from the alcohol using the procedure described for 18. 49; mp 35–37° C.

1-(Oxazolo[4,5-b]pyridin-2-yl)-1-oxo-hexane (48): This material was prepared in 70% yield from the alcohol using the procedure described for 18. 48; mp 51–53° C.

1-(Oxazolo[4,5-b]pyridin-2-yl)-1-oxo-heptane (47): This material was prepared in 64% yield from the alcohol using the procedure described for 18. 47; mp 52–53° C.

1-(Oxazolo[4,5-b]pyridin-2-yl)-1-oxo-octane (46): This material was prepared in 54% yield from the alcohol using the procedure described for 18. 46; mp 60–61° C.

1-(Oxazolo[4,5-b]pyridin-2-yl)-1-oxo-decane (45): This material was prepared in 61% yield from the alcohol using the procedure described above for compound 18. 45; mp 60–62° C.

1-(Oxazolo[4,5-b]pyridin-2-yl)-1-oxo-dodecane (44): This material was prepared in 94% yield from the alcohol using the procedure described for 18. 44; mp 68–69° C.

1-(Oxazolo[4,5-b]pyridin-2-yl)-1-oxo-tetradecane (43): This material was prepared in 72% yield from the alcohol using the procedure described above for compound 18. 43; mp 73–74° C.

1-(Oxazolo[4,5-b]pyridin-2-yl)-1-oxo-6-phenylhexane (53): This material was prepared in 78% yield from the alcohol using the procedure described for 18. 53; mp 61–63° C.

1-(Oxazolo[4,5-b]pyridin-2-yl)-1-oxo-7-phenylheptane (54): This material was prepared in 74% yield from the alcohol using the procedure described for 18. 54; mp 60–61° C.

1-(Oxazolo[4,5-b]pyridin-2-yl)-1-oxo-8-phenyloctane (55): This material was prepared in 72% yield from the alcolol using the procedure described above for compound 18. 55; mp 70–73° C.

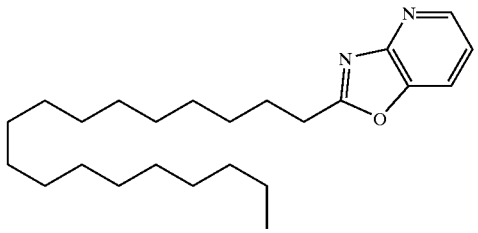

1-(Oxazolo[4,5-b]pyridin-2-yl)octadecane (61): This material was prepared in 30% yield from 1-cyanooctadecane (Mangold, H. K., et al., (1976) *Chem. Phys. Lipids* 17, 176–181) and 2-amino-3-hydroxypyridine using Method C3: mp 84–85° C.

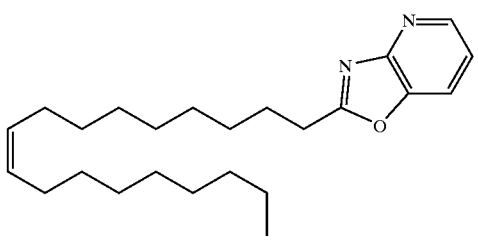

1-(Oxazolo[4,5-b]pyridin-2-yl)-9(Z)-octadecene (62): This material was prepared in 25% yield from 1-cyano-9 (Z)-octadecene (Baumann, W. J. et al., (1968) *J. Lipid Res.* 9, 287) and 2-amino-3-hydroxypyridine using Method C3.

What is claimed is:

1. An inhibitor of fatty acid amide hydrolase represented by the following formula:

A—B—C wherein:
  A is an α-keto heterocyclic pharmacophore for inhibiting the fatty acid amide hydrolase;
  B is a chain for linking A and C, said chain having a linear skeleton with a length of between 3 and 9 sequential atoms selected from the group consisting of carbon, oxygen, and sulfur, said linear skeleton being a linear alkyl diradical, optionally including one or more ether oxygens, and optionally including one or more thio ether sulfurs, the linear skeleton having a first end and a second end, the first end being covalently bonded to the α-keto group of A, with the following proviso:
    if the first end of said chain is an α-carbon with respect to the α-keto group of A, then the α-carbon is optionally mono- or bis-functionalized with substituents selected from the group consisting of fluoro, chloro, hydroxyl, alkoxy, trifluoromethyl, and alkyl; and
  C is an activity enhancer for enhancing the inhibition activity of said α-keto heterocyclic pharmacophore, said activity enhancer having at least one π-unsaturation situated within a π-bond containing radical selected from a group consisting of aryl, alkenyl, alkynyl, and ring structures having at least one unsaturation, with or without one or more heteroatoms, said activity enhancer being covalently bonded to the second end of the linear skeleton of B, no π-unsaturation within the π-bond containing radical being separated from the α-keto group of A by a sequence of less than 3 atoms bonded sequentially to one another, inclusive of said linear skeleton, at least one π-unsaturation within the π-bond containing radical being separated from the α-keto group of A by a sequence of no more than 9 atoms bonded sequentially to one another, inclusive of said linear skeleton;

wherein A is represented by the formula:

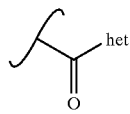

wherein "het" is selected from the following group:

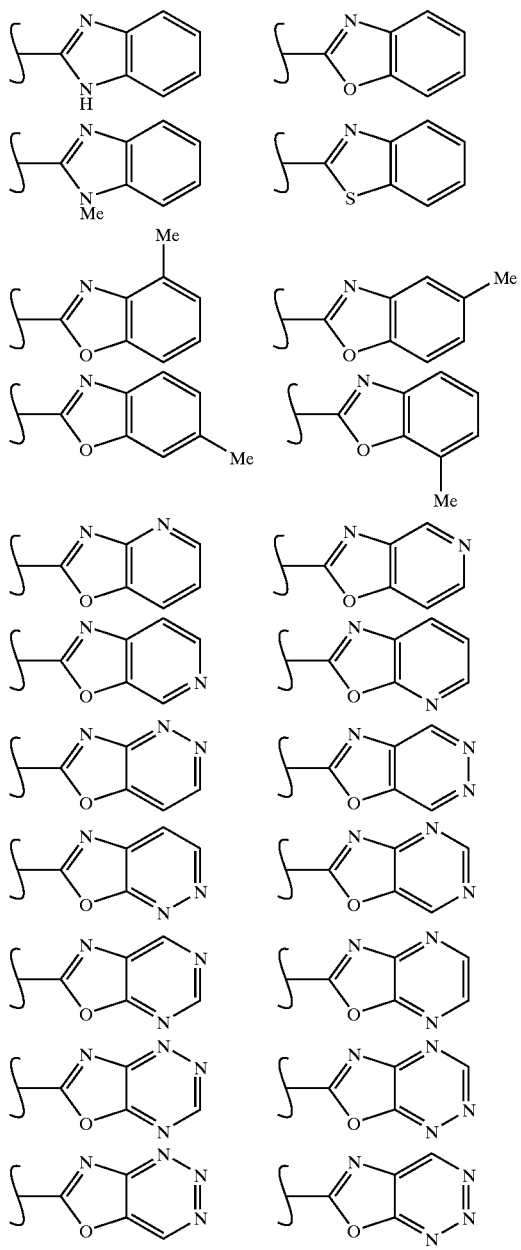

-continued

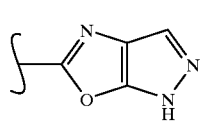 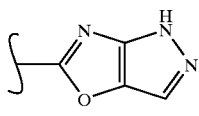

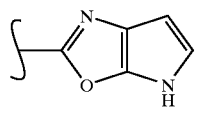 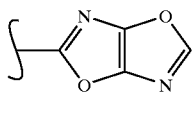

2. An inhibitor of fatty acid amide hydrolase according to claim 1 wherein "het" is selected from the following group:

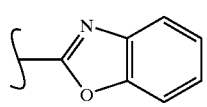 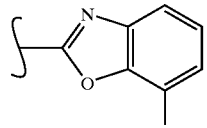

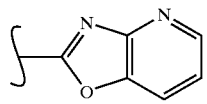 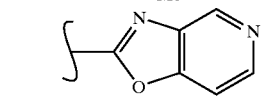

-continued

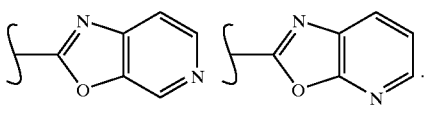

3. An inhibitor of fatty acid amide hydrolase according to claim 2 represented by the following structure:

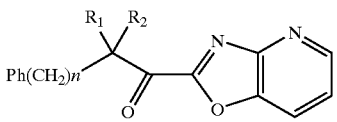

wherein $R_1$ and $R_2$ are independently selected from the group consisting of hydrogen, fluoro, chloro, hydroxyl, alkoxy, trifluoromethyl, and alkyl; and "n" is an integer between 2 and 7.

* * * * *